United States Patent [19]
Martin et al.

[11] Patent Number: 6,127,427
[45] Date of Patent: Oct. 3, 2000

[54] METALLOPROTEINASE INHIBITORS

[75] Inventors: Fionna Mitchell Martin; Christopher Norman Lewis; Mark Whittaker, all of Oxford, United Kingdom

[73] Assignee: British Biotech Pharmaceuticals Limited, Oxford, United Kingdom

[21] Appl. No.: 09/068,891

[22] PCT Filed: Nov. 21, 1996

[86] PCT No.: PCT/GB96/02877

§ 371 Date: May 22, 1998

§ 102(e) Date: May 22, 1998

[87] PCT Pub. No.: WO97/19053

PCT Pub. Date: May 29, 1997

[30] Foreign Application Priority Data

Nov. 23, 1995 [GB] United Kingdom .................... 9523937
May 24, 1996 [GB] United Kingdom .................... 9610985

[51] Int. Cl.[7] .......................... A61K 31/04; A61K 31/02; C07D 207/40
[52] U.S. Cl. .......................... 514/740; 514/740; 514/741; 562/621; 562/622; 548/545
[58] Field of Search .................... 562/621, 622; 548/545; 514/740, 741

[56] References Cited

U.S. PATENT DOCUMENTS 4,599,361 7/1986 Dickens et al. .
5,691,382 11/1997 Crimmin et al. ................ 514/575

FOREIGN PATENT DOCUMENTS 0489 577 A1 6/1992 European Pat. Off. .
90/05716 5/1990 WIPO .
WO 95/19956 7/1995 WIPO .

*Primary Examiner*—Alan L. Rotman
*Assistant Examiner*—Rita Desai
*Attorney, Agent, or Firm*—Banner & Witcoff, Ltd.

[57] ABSTRACT

Compounds of general formula (I)

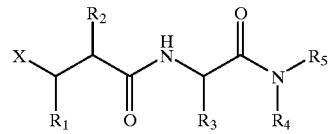

wherein X ia a —$CO_2H$, —NH(OH)CHO or —CONHOH group; $R_1$ is a cylcoalkyl, cycloalkenyl or non-aromatic heterocyclic ring containing up to 3 heteroatoms, any of which may be (i) substituted by one ore more substituents selected from $C_1$–$C_6$ alkyl, $C_2$–$C_6$ alkenyl, halo, cyano (—CN), —$CO_2H$, —$CO_2R$, —$CONH_2$, —CONHR, —$CON(R)_2$, —OH, —OR, oxo-, —SH, —SR, —NHCOR, and —$NHCO_2R$ wherein R is $C_1$–$C_6$ alkyl or benzyl and/or (ii) fused to a cycloalky or heterocyclic ring; and $R_2$, $R_3$, $R_4$ and $R_5$ are as defined in specification are matrix metalloproteinase inhibitors.

17 Claims, No Drawings

METALLOPROTEINASE INHIBITORS

CROSS REFERENCE

This application is a 371 of PCT/GB96/02877 filed Nov. 21, 1996.

The present invention relates to therapeutically active hydroxamic acid. N-formyl-N-hydroxyamino and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND OF THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site at the active site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. Chapman et al. (J. Med. Chem. 1993, 36, 4293–4301) report some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Three known classes of pseudopeptide or peptide mimetic MMP inhibitors have a hydroxamic acid group, N-formyl-N-hydroxyamino or a carboxylic group respectively as their zinc binding groups. With a few exceptions, such known MMPs may be represented by the structural formula (I)

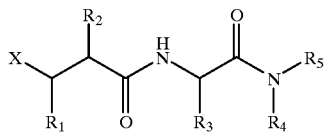

(I)

in which X is the zinc binding hydroxamic acid (—CONHOH), N-formyl-N-hydroxyamino (—NH(OH)CHO) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X interacts with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1-C_6)$ alkyl group (such as isobutyl) at $R_2$ may be preferred for activity against collagenase whilst a phenylalkyl group (such as phenylpropyl) at $R_2$ may provide selectivity for gelatinase over the other metalloproteinases.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, AIDS, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

As mentioned above MMP inhibitors have been proposed with hydroxamic acid, N-formyl-N-hydroxyamino or carboxylic acid zinc binding groups. The following patent publications disclose such MMP inhibitors:

| US 4599361 | (Searle) |
| EP-A-2321081 | (ICI) |
| EP-A-0236872 | (Roche) |
| EP-A-0274453 | (Bellon) |
| WO 90/05716 | (British Biotech) |
| WO 90/05719 | (British Biotech) |
| WO 91/02716 | (British Biotech) |
| WO 92/09563 | (Glycomed) |
| US 5183900 | (Glycomed) |
| US 5270326 | (Glycomed) |
| WO 92/17460 | (SB) |
| EP-A-0489577 | (Celltech) |
| EP-A-0489579 | (Celltech) |
| EP-A-0497192 | (Roche) |
| US 5256657 | (Sterling) |
| WO 92/13831 | (British Biotech) |
| WO 92/22523 | (Research Corp) |
| WO 93/09090 | (Yamanouchi) |
| WO 93/09097 | (Sankyo) |
| WO 93/20047 | (British Biotech) |
| WO 93/24449 | (Celltech) |
| WO 93/24475 | (Celltech) |
| EP-A-0574758 | (Roche) |
| EP-A-0575844 | (Roche) |
| WO 94/02446 | (British Biotech) |
| WO 94/02447 | (British Biotech) |
| WO 94/21612 | (Otsuka) |
| WO 94/21625 | (British Biotech) |
| WO 94/24140 | (British Biotech) |
| WO 94/25434 | (Celltech) |
| WO 94/25435 | (Celltech |
| WO 95/04033 | (Celltech) |
| WO 95/04735 | (Syntex) |
| WO 95/04715 | (Kanebo) |
| WO 95/06031 | (Immunex) |
| WO 95/09841 | (British Biotech) |
| WO 95/12603 | (Syntex) |
| WO 95/19956 | (British Biotech) |
| WO 95/19957 | (British Biotech) |
| WO 95/19961 | (British Biotech) |
| WO 95/19965 | (Glycomed) |
| WO 95/22966 | (Sanofi Winthrop) |
| WO 95/23790 | (SB) |

BRIEF DESCRIPTION OF THE INVENTION

The present invention makes available a novel class of MMP inhibitors of the general structure (I) above with a hydroxamic acid, N-formyl-N-hydroxyamino or carboxylic acid zinc binding group X, principally characterised by the presence of a cycloalkyl, cycloalkenyl or non-aromatic heterocyclic group as substituent $R_1$. Compounds of the new class have good inhibitory potencies against various MMP enzymes, particularly collagenases and stromelysins. The class includes compounds with appropriate aqueous solubility, pKa, log P and molecular weight for good oral absorption. Also within the class are compounds which are effective in inhibiting release of TNF from cells.

The patent publications listed above relating to hydroxamic and carboxylic acid based MMP inhibitors, disclose MMP inhibitors having a variety of groups $R_1$, but none suggests or discloses compounds with $R_1$=cycloalkyl, or cycloalkenyl, nor the inhibitory, physicochemical or pharmacokinetic properties which might be expected of such compounds. WO 95/19956 does disclose compounds wherein $R_1$=non-aromatic heterocyclic, but in such cases $R_4$ is substituted or unsubstituted phenyl or heteroaryl.

DETAILED DESCRIPTION OF THE INVENTION

The present invention provides compounds of general formula (I)

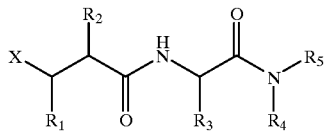

(I)

wherein:

X is a —$CO_2H$, —NH(OH)CHO or —CONHOH group;

$R_1$ is a cycloalkyl, cycloalkenyl or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R$, —$CONH_2$, —CONHR, —CON(R)$_2$, —OH, —OR, oxo-, —SH, —SR, —NHCOR, and —NHCO$_2$R wherein R is $C_1$–$C_6$ alkyl or benzyl and/or (ii) fused to a cycloalkyl or heterocyclic ring;

$R_2$ is a $C_1$–$C_{12}$ alkyl, $C_2$–$C_{12}$ alkenyl, $C_2$–$C_{12}$ alkynyl, phenyl($C_1$–$C_6$ alkyl)-, heteroaryl($C_1$–$C_6$ alkyl)-, cycloalkyl($C_1$–$C_6$ alkyl)-, cycloalkenyl($C_1$–$C_6$ alkyl)-, phenoxy($C_1$–$C_6$ alkyl)-, heteroaryloxy($C_1$–$C_6$ alkyl)-, phenyl($C_1$–$C_6$ alkyl)O($C_1$–$C_6$ alkyl)-, heteroaryl($C_1$–$C_6$ alkyl)O($C_1$–$C_6$ alkyl)-, phenyl($C_1$–$C_6$ alkyl)S($C_1$–$C_6$ alkyl)-, or heteroaryl($C_1$–$C_6$ alkyl)S($C_1$–$C_6$ alkyl)- group, any one of which may be optionally substituted by $C_1$–$C_6$ alkyl, $C_1$–$C_6$ alkoxy, halo, cyano (—CN), phenyl, substituted phenyl or heteroaryl.

$R_3$ is the characterising group of a natural or non-natural a amino acid in which any functional groups may be protected;

$R_4$ is (a) an optionally substituted cycloalkyl or cycloalkenyl ring or (b) (except in the case where $R_1$ is a substituted or unsubstituted non-aromatic heterocyclic ring as defined above in relation to $R_1$) a heteroaryl ring which may be fused to a benzene or heteroaryl ring, either or both of which rings may be substituted, and in which any ring nitrogen atom may be oxidised as an N-oxide, or (c) a group —CHR$^x$R$^y$ wherein R$^x$ and R$^y$ each independently represents an optionally substituted phenyl or heteroaryl ring which may be linked covalently to each other by a bond or by a $C_1$–$C_4$ alkylene or $C_2$–$C_4$ alkenylene bridge, or (d) a group of formula —(Z—O)$_n$—Z wherein Z is straight or branched $C_1$–$C_6$ alkyl optionally interrupted by one or more non-adjacent S and/or N atoms, n is an integer >1, and no continuous linear sequence of atoms in the group $R_4$ is >12, or (e) a straight or branched $C_1$–$C_6$ alkyl group, optionally interrupted by one or more non-adjacent S and/or N atoms, which is substituted by at least two substituents of formula —(Z)$_p$—(OZ)$_q$ wherein Z is straight or branched $C_1$–$C_6$ alkyl optionally interrupted by one or more non-adjacent S and/or N atoms, p is 0 or 1, q is 1 or 2, and no continuous linear sequence of atoms in the group $R_4$ is >12, or (f) hydrogen, $C_1$–$C_6$ alkyl, $C_1$–$C_4$ perfluoroalkyl, or a group D-($C_1$–$C_6$ alkyl)- wherein D is hydroxy, $C_1$–$C_6$ alkoxy, $C_1$–$C_6$ alkylthio, acylamino, optionally substituted phenyl or 5- or 6-membered heteroaryl, $NH_2$, or mono- or di-($C_1$–$C_6$ alkyl) amino; or $R_3$ and $R_4$ taken together represent a divalent chain of formula —C($R^a$)($R^b$)—A—Alk— wherein $R^a$ and $R^b$ are independently hydrogen or $C_1$–$C_6$ alkyl. A is a bond, —O—, —S—, —S—S—, —NH— or —$NR^a$— wherein $R^a$ is $C_1$–$C_6$ alkyl, and Alk is $C_1$–$C_6$ alkylene;

$R_5$ is hydrogen or a $C_1$–$C_6$ alkyl group;

or a salt, hydrate or solvate thereof.

The term "cycloalkyl" as used herein means a saturated alicyclic ring having from 3–8 carbon atoms and includes, for example, cyclohexyl, cyclooctyl, cycloheptyl, cyclopentyl, cyclobutyl, and cyclopropyl.

The term "cycloalkenyl" as used herein means an unsaturated alicyclic ring having from 5–8 carbon atoms and includes, for example, cyclohexenyl, cyclooctenyl, cycloheptenyl, and cyclopentenyl. The ring may contain more than one double bond.

The unqualified term "heterocyclic" or "heterocyclyl" as used herein means (i) a 3–8 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin4-yl, 3-methyl-2,5-dioxo-1-imidazolidinyl and 3,4,4-trimethyl-2,5-dioxo-1-imidazolidinyl, or (ii) a naphththalimido (ie 1, 3-dihydro-1, 3-dioxo-2H-benz[f]isoindol-2-yl), 1,3-dihydro-1-oxo-2H-benz[f]isoindol-2-yl, 1, 3-dihydro- 1, 3-dioxo-2H-pyrrolo[3, 4-b]quinolin-2-yl, or 2,3-dihydro-1, 3-dioxo-1 H-benz[d,e] isoquinolin-2-yl group.

The term "non-aromatic heterocyclic ring" means a 5–7 membered heterocyclic ring containing one, two or three heteroatoms selected from S, N and O in which at least two adjoining atoms are saturated. Examples include morpholinyl, thiomorpholinyl, dihydrofuranyl, tetrahydrothienyl, dihydrothienyl, piperidinyl, pyrrolidinyl, pyrrolinyl, dioxolanyl, oxathiolanyl, imidazolinyl, imidazolidinyl, pyrazolinyl, pyrazolidinyl, pyranyl, dioxanyl, dithianyl, oxathianyl, and piperazinyl.

The term "heteroaryl" means a 5–7 membered aromatic heterocyclic ring containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with a phenyl group or up to four substituents, each of which independently may be ($C_1$–$C_6$) alkoxy, hydroxy, mercapto, ($C_1$–$C_6$)alkylthio, amino, halo (including fluoro, chloro, bromo and iodo), cyano, trifluoromethyl, nitro, —COOH, —$CONH_2$, —$CONHR^A$ or —$CONR^A R^A$ wherein $R^A$ is a ($C_{1-C6}$)alkyl group or the residue of a natural alpha-amino acid.

The term "side chain of a natural or non-natural alpha-amino acid" means the group R in a natural or non-natural amino acid of formula $NH_2$—CH(R)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$–$C_6$ alkyl ester), amino groups may be converted to amides (for example as a $NHCOC_1$–$C_6$ alkyl amide) or carbamates (for example as an NHC(=O) $OC_1$–$C_6$ alkyl or NHC(=O)$OCH_2$Ph carbamate), hydroxyl groups may be converted to ethers (for example an $OC_1$–$C_6$ alkyl or a O($C_1$–$C_6$ alkyl)phenyl ether) or esters (for example a OC(=O)$C_1$–$C_6$ alkyl ester) and thiol groups may be converted to thioethers (for example a tert-butyl or benzyl thioether) or thioesters (for example a SC(=O)$C_1$–$C_6$ alkyl thioester).

Examples of side chains of non-natural alpha amino acids include those referred to below in the discussion of suitable $R_3$ groups for use in compounds of the present invention.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X groups—S,

C atom carrying the $R_2$ group—R.

C atom carrying the $R_3$ group—S, but mixtures in which the above configurations predominate are also contemplated.

In the compounds of the invention the group $R_1$ may be, for example. cyclohexyl, 4-methylcyclohexyl, cyclooctyl, cycloheptyl, cyclopentyl, cyclobutyl, cyclopropyl, tetrahydropyranyl, tetrahydrothien-3-yl, 1,1 -dioxo-tetrahydrothien-3-yl, N-acetylpiperidin-4-yl, N-methylpiperidin-4-yl or morpholin-4-yl. Particularly preferred at present are the cases where $R_1$ is cyclopentyl, cyclohexyl and cyclopropyl.

As previously stated, the compounds of the present invention are principally distinguished from the compounds disclosed in the prior patent publications listed above by the identity of the group $R_1$. Accordingly the groups $R_2$, $R_3$, $R_4$, and $R_5$ may include those which have been disclosed in the corresponding positions of compounds disclosed in any of those prior art patent publications listed above. Without limiting the generality of the foregoing, examples of substituents $R_2$, $R_3$, $R_4$, and $R_5$ are given below:

$R_2$ may for example be $C_1$–$C_{12}$ alkyl, $C_3$–$C_6$ alkenyl, phenyl($C_1$–$C_6$ alkyl)- or phenoxy($C_1$–$C_6$ alkyl) optionally substituted in the phenyl ring by halogen, $C_1$–$C_6$ alkyl, $C_1$–$C_6$ alkoxy or phenyl. Specific examples of such groups include iso-butyl, n-pentyl, n-hexyl, n-heptyl, n-octyl, n-nonyl, n-decyl, phenylpropyl, 4-chlorophenylpropyl, 4-methylphenylpropyl, 4-methoxyphenylpropyl, 4-phenyl-phenylpropyl and phenoxybutyl. Presently preferred are compounds in which $R_2$ is iso-butyl, n-octyl, benzyloxypropyl, phenoxybutyl or 4-phenyl-phenylpropyl.

$R_3$ may for example be $C_1$–$C_6$ alkyl, benzyl, 2,- 3-, or 4-hydroxybenzyl, 2,- 3-, or 4-benzyloxybenzyl, 2,- 3-, or 4-$C_1$–$C_6$ alkoxybenzyl, or benzyloxy($C_1$–$C_6$alkyl)- group; or the characterising group of a natural α amino acid, in which any functional group may be protected, any amino group may be acylated and any carboxyl group present may be amidated; or a group —[Alk]$_n$R$_6$ where Alk is a ($C_1$–$C_6$)alkyl or ($C_2$–$C_6$)alkenyl group optionally interrupted by one or more —O—, or —S— atoms or —N($R_7$)— groups [where $R_7$ is a hydrogen atom or a ($C_1$–$C_6$)alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$) alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:

each of R$_a$, R$_b$ and R$_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl; or R$_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, ($C_1$–$C_4$)perfluoroalkyl, —CH$_2$OH, —CO$_2$ ($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —SO$_2$($C_1$–$C_6$) alkyl, —S($C_2$–$C_6$)alkenyl, —SO($C_2$–$C_6$)alkenyl, —SO$_2$($C_2$–$C_6$)alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl. ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH ($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$) alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$) alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl.

Examples of particular $R_3$ groups include benzyl, isobutyl, tert-butyl, 1-fluoro-1-methylethyl, 1-hydroxy-1-methylethyl, 1-methoxy-1-methylethyl, 1-benzylthio-1-methylethyl, 1-methylthio-1-methylethyl and 1-mercapto-1-methylethyl. Presently preferred are compounds in which $R_3$ is t-butyl or 1-mercapto-1-methylethyl.

$R_4$ may for example be cyclopropyl, cyclobutyl, cyclopentyl, cyclohexyl cycloheptyl, cyclooctyl or adamantyl;

optionally substituted phenyl, napthyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, benzimidazolyl, benzotriazolyl, pyrazinyl, pyridazinyl, pyrimidinyl, dithianyl, benzo[b] thienyl, isoxazolyl or quinolinyl. Examples of particular $R_4$ groups of this type include phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonylmethylthiazol-2-yl, 4-phenylthiazol-2-yl, 4, 5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-2-yl, 1,2,4-oxadiazol-3-yl, 1,3,4-oxadiazol-2-yl, 1,2,4-thiadiazol-5-yl, 3-phenyl-1, 2,4-thiadiazol-5-yl, 1,3,4-thiadiazol-2-yl, 5-methyl-1, 3,4-thiadiazol-2-yl, pyridin-2-yl, pyridin-3-yl, pyridin-4-yl, N-oxides of pyridin-2-yl pyridin-3-yl and pyridin4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, quinolin-3-yl. Presently preferred are compounds in which $R_4$ is phenyl, 3-methoxyphenyl, pyridin-2-yl, pyridin-3-yl, and thiazol-2-yl, 4,5-dimethylthiazol-2-yl, 5-bromothiazol-2-yl, 4-ethoxycarbonylmethylthiazol-2-yl, 5-methyl-1,3,4-thiadiazol-2-yl or 4-tertbutylthiazol-2-yl. Particularly preferred $R_4$ groups of this type are 3-methoxyphenyl, pyridin-2-yl, pyridin-3-yl, thiazol-2-yl, 4-ethoxycarbonylmethylthiazol-2-yl, 5-methyl-1,3,4-thiadiazol-2-yl or 4-tert-butylthiazol-2-yl;

- a group —$CHR^xR^y$ wherein $R^x$ and $R^y$ independently represent optionally substituted phenyl, thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinolyl, pyrimidinyl, piperazinyl or triazinyl. Examples of particular $R^x$ and $R^y$ include phenyl and 4-chlorophenyl. Where $R^x$ and $R^y$ are linked covalently, an example of a group $R_4$ is 9-H-fluoren-9-yl;

- a polyether chain possessing at least two non-adjacent oxygen atoms, for example 2-(2-methoxyethoxymethoxy)ethyl, 1, 1 -dimethyl-2-(2-methoxyethoxymethoxy)ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy)propyl, 2,2-dimethyl-3-(2-methoxyethoxymethoxy)propyl, 2-(2-methoxyethoxy)ethyl, 3-(2-methoxyethoxy)propyl, 2-methyl-2,2-d i(2-methoxyethyl)propyl, 2-methyl-2,2-di(2-methoxyethyl)butyl, and 2-methyl-2,2-di(2-methoxymethyl)propyl. A presently preferred $R_4$ group of this type is 2-(2-methoxyethoxy)ethyl;

- hydrogen, methyl, ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl eg 2-phenyl-2-methyleth-2-yl, phenylpropyl, phenylbutyl, or phenylpentyl. Presently preferred $R_4$ groups of this type are hydrogen or methyl.

Where $R_3$ and $R_4$ taken together represent a divalent chain of formula —$C(R^a)(R^b)$—A—Alk— wherein $R^a$ and $R^b$ are independently hydrogen or $C_1$–$C_6$ alkyl, A is a bond, —O——S—, —S—S—, —NH— or —$NR^a$— wherein $R^a$ is $C_1$–$C_6$ alkyl, and Alk is $C_1$–$C_6$ alkylene, examples of such divalent chains include —$C(CH_3)_2SCH_2CH_2CH_2$—, and —$C(CH_3)_2SSCH_2CH_2$—.

$R_5$ may for example be hydrogen, methyl or ethyl. Presently preferred are compounds in which $R_5$ is hydrogen.

An example of a specific compound of the invention which is presently preferred for its activity in inhibiting TNF release from cells, and for its activity as a broad spectrum MMP inhibitor, is 2S-cyclopentyl-$N^4$-[2,2-dimethyl-1S-(methylcarbamoyl)propyl)]-$N^1$-hydroxy-3R-isobutylsuccinamide, and salts solvates and hydrates thereof.

Other interesting compounds of the invention include those disclosed in Examples 1, 3–17, and 19–33 herein, and their salts hydrates and solvates.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises causing an acid of general formula (II)

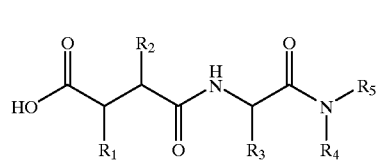

(II)

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$ Conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-$N^1$-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

Compounds according to the present invention in which X is a carboxylic acid group —COOH, ie compounds of formula (II) above, may be prepared by a process comprising: coupling an acid of formula (III) or an activated derivative thereof with an amine of formula (IV)

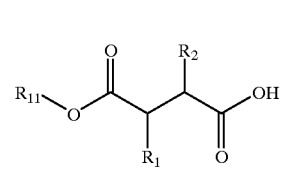

(III)

-continued (IV)

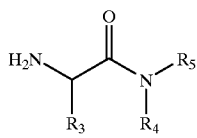

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, $R_4$, and $R_5$.

Active derivatives of acids (III) include activated esters such as the pentafluorophenyl ester, acid anhydrides and acid halides, eg chlorides. Suitable hydroxy protecting groups may be selected from those known in the art.

Amino acid amides of formula (IV) are either known or are prepared by routine known synthetic methods. Compounds of formula (III) may be prepared by one or more of the following routes:

Route 1: By Ireland-Claisen rearrangement of compounds of formula (V) to products (VI)

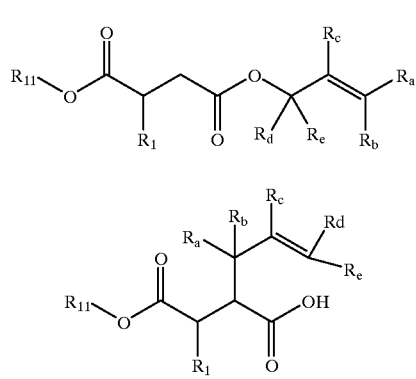

in which formulae $R_1$ and $R_{11}$ have the meanings ascribed to them in formula (III), and $R_a$–$R_e$ are substituents selected so that the partial structure (VII)

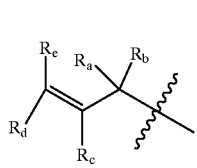

corresponds to the desired $R_2$ substituent in compound (III).

Claisen rearrangement of allyl enol ethers is useful for stereocontrolled carbon-carbon bond formation (for recent reviews see P. Wipf in *Comprehensive Organic Synthesis*, Vol. 5 (Eds.: B. M. Trost, I. Fleming, L. A. Paquette) Pergamon, New York, 1991, p 827; S. Blechert, Synthesis, 1989, 71; F. E. Zeigler, Chem. Rev., 1988, 88, 1423). Among the available methods for effecting this [3,3] sigmatropic rearrangement is the Ireland-Claisen procedure, by which a silyl ketene acetal of an allyl ester can be converted to an a-allyl carboxylic acid. A particularly important aspect of the Ireland Claisen rearrangement is that, through efficient control of ketene acetal geometry, a highly reliable transfer of stereochemistry from starting material to product can be realised (R. E. Ireland, P. Wipf and J. D. Armstrong, J. Org. Chem. 1991, 56, 650; ibid 56, 3572).

The rearrangement may be effected in an aprotic solvent such as tetrahydrofuran, by first converting the substituted allyl ester (V) to the enol form, for example by treatment with a strong organic base, such as lithium diisopropylamine, followed by silylation of the enol hydroxy group, using a silylating agent (eg trimethylsilyl chloride, triethylsilyl chloride, tripropylsilyl chloride, tert-butyidimethylsilyl chloride, or tert-butyidiphenylsilyl chloride). The resultant silyl ketene acetal then undergoes the desired rearrangement to produce the readily hydrolysable silyl ester of compound (V). In the foregoing procedure, enolisation and silylation are preferably effected at low temperature, eg –70° C. or lower, and the rearrangement may be induced by raising the temperature, eg to about 4° C. to 55° C.

The allylic double bond of product (VI) of the rearrangement of (V) may be reduced, for example by catalytic hydrogenation, to form compounds (VIA), in which $R_1$ and $R_{11}$ have the meanings ascribed to them in formula (III), and $R_a$–$R_e$ are substituents selected so that the partial structure (VIIA)

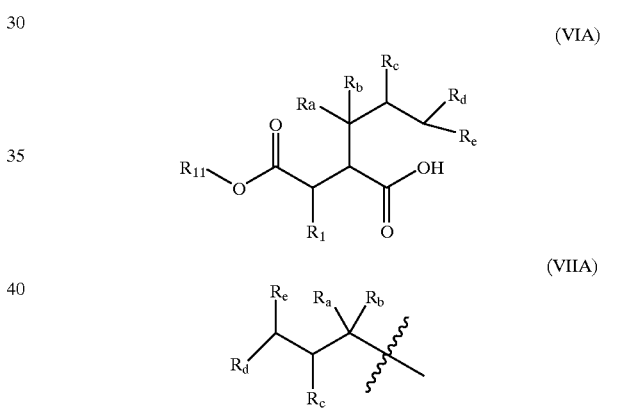

corresponds to the desired $R_2$ substituent in compound (III).

This Route 1 to compounds (III) involving rearrangement of compounds (IV) to (V), possibly followed by reduction of the allylic double bond, represents a novel application of the Ireland-Claisen rearrangement to the synthesis of 2,3-disubstituted succinates.

Route 2: By Ireland-Claisen rearrangement (as discussed above in relation to Route 1 of compounds of formula (VIII) to products (IX)

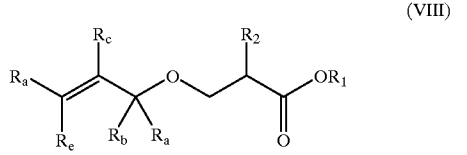

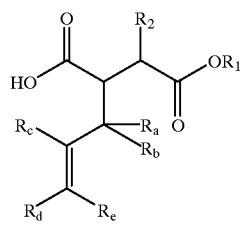
(IX)

in which formulae $R_2$ and $R_{11}$ have the meanings ascribed to them in formula (III), and $R_a$–$R_e$ are substituents selected so that the partial structure (VII)

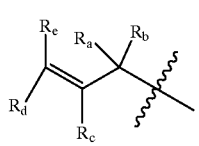
(VII)

corresponds to the desired $R_1$ substituent in compound (III). In this instance, the groups $R_a$ and $R_d$ are linked to form part of the desired alicyclic or heterocyclic ring, $R_1$. Again the double bond in partial structure (VI) of product (IX) may be reduced to form compounds (IXA)

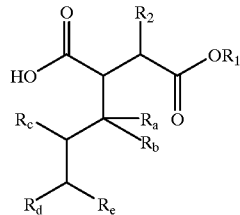
(IXA)

in which $R_1$ and $R_{11}$ have the meanings ascribed to them in formula (III), and $R_a$–$R_e$ are substituents selected so that the partial structure (VIIA) corresponds to the desired $R_1$ substituent in compound (III).

This Route 2 to compounds (III) involving rearrangement of compounds (VIII) to (IX), possibly followed by reduction of the allylic double bond, represents a novel application of the Ireland-Claisen rearrangement to the synthesis of 2,3-disubstituted succinates.

Route 3: By alkylation of a succinate of formula (X) with an alkylating agent $R_1$-L, or by alkylation of a succinate of formula (XA) with an alkylating agent $R_2$-L, where L is a suitable leaving group such as chloride, bromide, iodide, triflate or mesylate,

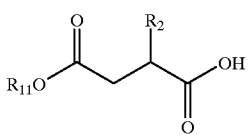
(X)

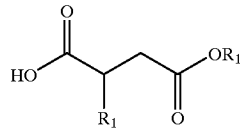
(XA)

wherein $R_1$, $R_2$, and $R_{11}$ are as defined in relation to formula (III) above.

Succinates of formula (V), (VI), (VIII), (IX), (X) and (XA) insofar as they are not known from the literature can be prepared, in homochiral form if desired, by methods known in the art. In the special case where $R_1$ is a nitrogen-containing heterocycle linked through a nitrogen atom, compounds of formula (III) may be prepared according to Route 1 from a suitably protected aspartic acid derivative (XI)

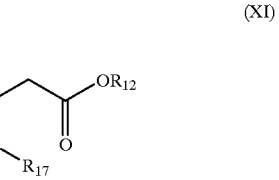
(XI)

wherein $R_1$, and $R_{12}$ are carboxyl protecting groups, and $R_{16}$ and $R_{17}$ taken together with the nitrogen atom to which they are attached form the desired nitrogen containing non-aromatic heterocyclic group $R_1$.

Compounds of the invention in which X is an N-formyl-N-hydroxyamino group may be prepared by deprotecting an N-protected N-formyl-N-hydroxyamino compound of formula (XII):

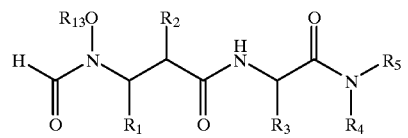
(XII)

in which $R_{21}$, $R_2$, $R_3$, $R_4$, and $R_5$ are as defined in general formula (I) and $R_{13}$ is a group convertible to a hydroxy group by hydrogenolysis or hydrolysis. Benzyl is a preferred $R_{13}$ group for removal by hydrogenolysis, and tetrahydropyranyl is a preferred group for removal by acid hydrolysis.

Compounds of formula (XII) may be prepared by a process comprising: causing an acid of formula (XIII) or an activated derivative thereof to react with an amine of formula (IV) as defined above

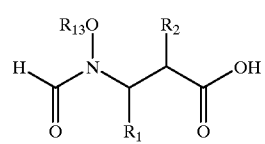
(XIII)

wherein $R_1$ and $R_2$ are as defined in general formula (I) except that any substituents in $R_1$ and $R_2$ which are potentially reactive in the coupling reaction may themselves be protected from such reaction, and $R_{13}$ is a group convertible to a hydroxy group by hydrogenolysis or hydrolysis as referred to in connection with formula (XII) above, and optionally removing protecting groups from $R_1$ and $R_2$, and from $R_3$, $R_4$, and $R_5$ in the amine (IV).

Compounds of formula (XIII) may be prepared by N-formylation, for example using acetic anhydride and formic acid, of compounds of formula (XIV)

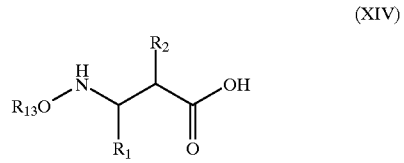

(XIV)

wherein $R_1$, $R_2$ and $R_{16}$ are as defined in relation to formula (XII).

As mentioned above, compounds of formula (I) are useful in human or veterinary medicine since they are active as inhibitors of MMPs, and a further advantage lies in their ability to inhibit the release of tumour necrosis factor (TNF) from cells.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs and/or TNF; and (iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases as well as neuroinflammatory disorders, including those involving myelin degradation, for example multiple sclerosis. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier. In view of the water-solubility, and oral bioavailability advantanges of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia: non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 5 to 100 mg of a compound of the invention. A suitable daily dose for a mammal may vary widely depending on the condition of the patient. However, a dose of a compound of general formula I of about 0.1 to 10 mg/kg body weight, particularly from about 0.1 to 3mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint.

Examples 1 and 3–33 which follow serve to illustrate embodiments of the invention:

The following abbreviations have been used throughout:

| DIPE | Diisopropyl ether |
| --- | --- |
| DMAP | 4-Dimethyl-aminopyridine |
| DMF | N,N-Dimethylformamide |
| EDC | N-Ethyl-N'-(3-dimethylaminopropyl)carbodiimide hydrochloride |
| HOBt | 1-Hydroxybenzotriazole |
| NMR | Nuclear magnetic resonance |
| NMM | N-methylmorpholine |
| NaHMDS | Sodium bis(trimethylsilyl)amide |
| TESCI | Chlorotriethylsilane |
| TFA | Trifluoroacetic acid |
| THF | Tetrahydrofuran |
| TLC | Thin layer chromatography |

$^1$H and $^{13}$C NMR spectra were recorded using a Bruker AC 250E spectrometer at 250.1 and 62.9 MHz, respectively. Elemental microanalyses were performed by either CHN Analysis Ltd., Alpha House, Countesthorpe Road, South Wigston, Leicester LE8 2PJ, UK, or MEDAC Ltd., Dept. of Chemistry, Brunel University, Uxbridge, Middlesex UB8 3PH, UK.

EXAMPLE 1

2S-Cyclopentyl-3R-[2,2-dimethyl-1S-(methylcarbamoyl)propylcarbamoyl]-5-methylhexanoic acid

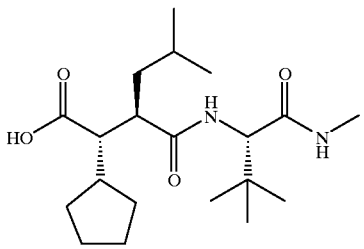

STEP A:

4R-Benzyl-3-cyclopentylacetyl-oxazolidin-2-one

Cyclopentyl acetic acid (59 ml, 470.4 mmol) was taken up in dry THF (1 l) and cooled to −78° C. under argon. Pivaloyl chloride (58 ml, 470.4 mmol) and triethylamine (85 ml, 611.5 mmol) were added and the reaction mixture stirred for 15 min at −78° C. and then warmed to 0° C. and stirred for 40 min before cooling back to −78° C. In a separate flask, 4R-benzyl-oxazolidin-2-one (100 g, 564.5 mmol) was dissolved in dry THF (1 l) and the solution was cooled to −78° C. under argon. To this stirred solution was added 2.5 M n-butyllithium in hexanes (226 ml, 565 mmol). After the addition was complete the resulting solution was cannulated into the former reaction flask and the mixture was stirred for a further 15 minutes at −78° C. before warming to room temperature and stirring overnight. The reaction was quenched by addition of 1 M potassium hydrogen carbonate solution (600 ml). The solvents were removed under reduced pressure and the residue was extracted into ethyl acetate (x3). The combined ethyl acetate extracts were washed with brine, dried over magnesium sulphate and filtered. The solution was concentrated under reduced pressure to give a yellow oil which crystallised on standing (139.8 g, including residual solvent). $^1$H-NMR; δ (CDCl$_3$), 7.37–7.20 (5H, m), 4.69 (1 H, m), 4.23–4.12 (2H. m), 3.30 (1H, dd, J=13.3, 3.3 Hz), 3.04 (1H, dd, J=16.6. 7.1 Hz), 2.91 (1H, dd, J=16.6, 7.1 Hz), 2.77 (1H, dd, J=13.3, 3.3 Hz), 2.34 (1H, m), 1.94–1.83 (2H, m), 1.69–1.52 (4H, m) and 1.30–1.14 (2H, m).

STEP B:

4-(4R-Benzyl-2-oxo-oxazolidin-3-yl-3R-cyclopentyl-4-oxo-butyric acid tert-butyl ester 4R-Benzyl-3-cyclopentylacetyl-oxazolidin-2-one (Step A) (135 g, 469.8 mmol) was dissolved in dry THF (2 l) and the solution was cooled to −78° C. under argon. To this cooled solution was added a 1.0 M solution NaHMDS in THF (705 ml, 705 mmol). The resulting mixture was stirred for a further 1 hour at −78° C., tert-butyl bromoacetate (114 ml, 705 mmol) was added and the reaction mixture was then stored in the freezer (−20° C.) for 48 hours. A saturated solution of ammonium chloride (500 ml) was added and the solvent was removed under reduced pressure. The resulting aqueous residue was extracted into ethyl acetate (x3). The ethyl acetate extracts were combined, washed with brine, dried over magnesium sulphate, filtered and evaporated under reduced pressure to give a white solid. Recrystallisation from ethyl acetate/hexane gave the desired product (98.5 g, 52%). $^1$H-NMR; δ (CDCl$_3$), 7.38–7.23 (5H, m), 4.67 (1 H, m), 4.25 (1 H, m), 4.15–4.13 (2H, m), 3.38 (1H, dd, J=13.5, 3.2 Hz), 2.86 (1H, dd, J=16.8, 11.2 Hz), 2.73 (1H, dd, J =13.5, 11.2 Hz), 2.53 (1H, dd, J=16.8, 3.2 Hz), 2.00 (1H, m), 1.83–1.44 (6H, m), 1.42 (9H, s) and 1.41–1.17 (2H, m).

STEP C:

2R-Cyclopentylsuccinic acid 1-benzyl ester 4-tert-butyl ester

Benzyl alcohol (40 ml, 386.1 mmol) was dissolved in dry THF (800 ml) and the solution was placed under argon and cooled to −5° C. using a methanol/ice bath. To this stirred solution was added 2.5M n-butyllithium in hexanes (116 ml, 290 mmol) slowly over a period of 45 minutes, so that the temperature remained below 0° C. throughout the addition. After the addition was complete, the reaction mixture was stirred for a further 40 minutes at −5° C. Separately, a solution of 4-(4R-benzyl-2-oxo-oxazolidin-3-yl-3R-cyclopentyl-4-oxo-butyric acid tert-butyl ester (Step B) (77.9 g, 193 mmol) in dry THF (400 ml) was placed under argon, cooled to −5° C. and cannulated into the former reaction flask and the mixture was stirred for a further 15 minutes at −5° C., before warming to room temperature and stirring overnight. The reaction was quenched with saturated ammonium chloride solution (450 ml), the solvents were removed under reduced pressure and the residue was extracted with ethyl acetate (x2). The combined organic extracts were washed with brine, dried over anhydrous magnesium sulphate and filtered. The filtrate was concentrated under reduced pressure to give a clear oil which was purified by column chromatography (silica gel, 20% ethyl acetate in hexane) to give the title compound as a clear oil (40.9 g, 86%). $^1$H-NMR; δ (CDCl$_3$), 7.45–7.29 (5H, m), 5.19 (2H, m), 2.92–2.73 (2H, m), 2.49 (1H, m), 2.01 (1H, m), 1.84–1.49 (6H, m), 1.41 (9H, s) and 1.38–1.19 (2H, m).

STEP D:

2R-Cyclopentylsuccinic acid 1-benzyl ester

2R-Cyclopentyl-succinic acid 1-benzyl ester 4-tert-butyl ester (Step C) (36.43 g, 109.6 mmol) was dissolved in dichloromethane (300 ml) and TFA (200 ml) and the resulting solution was stored at 4° C. overnight. The solvents were removed under reduced pressure and the residue was azeotroped with toluene (x3) to give the product as a brown oil (30.30 g, quant). $^1$H-NMR: δ (CDCl$_3$), 11.50 (1 H, br s), 7.45–7.29 (5H, m), 5.19 (2H, m), 2.94–2.74 (2H, m), 2.60 (1H. m), 2.07 (1H, m), 1.84–1.52 (6H, m) and 1.38–1.22 (2H, m).

STEP E:

2R-Cyclopentylsuccinic acid 1-benzyl ester 4-(2-methylallyl) ester

2R-Cyclopentylsuccinic acid 1-benzyl ester (Step D) (23.5 g, 85 mmol) was dissolved in dichloromethane (200 ml) and EDC (19.5 g, 102 mmol), DMAP (200 mg, catalytic) and 2-methyl 2-propen-1-ol (7.5 ml, 89 mmol) were added. The resulting mixture was stirred at room temperature overnight. The solvent was removed under reduced pressure and the residue was dissolved in ethyl acetate. The organic solution was washed successively with 1 M hydrochloric acid, 1 M sodium carbonate and brine, then dried over magnesium sulphate and filtered. The solvent was removed under reduced pressure to leave an oil which was purified by column chromatography (silica gel, 20% ethyl acetate in hexane) to give the title compound as a colourless oil (21.4 g, 76%). $^1$H-NMR; δ (CDCl$_3$), 7.36–7.27 (5H, m), 5.19–5.07 (2H, m), 4.93 (2H, d, J=5.4 Hz), 4.46 (2H, s), 2.89–2.71 (2H, m), 2.58 (1H, m), 2.03 (1H, m), 1.73 (3H, s), 1.64–1.49 (6H, m), 1.36–1.16 (2H, m).

STEP F:

2S-Cyclopentyl-3 R-(2-methylallyl)succinic acid 4-benzyl ester

Diisopropylamine (29.3 ml, 209 mmol) was taken up in dry THF (700 ml) and cooled to −78° C. under argon before addition of a 2.3 M solution of butyllithium in hexanes (83.3 ml, 192 mmol). The reaction was allowed to warm briefly to −30° C. and then cooled back to −78° C. 2R-Cyclopentylsuccinic acid 1-benzyl ester 4-(2-methylallyl) ester (Step E) (57.54 g, 174 mmol) was added and the resulting mixture was stirred for 45 minutes. TESCl (32.2 ml, 192 mmol) was added and, after stirring for a further 30 minutes at −78° C., the reaction mixture was warmed to 55° C. and stirred overnight. The reaction was quenched by addition of 1M hydrochloric acid in methanol and the solvents were removed under reduced pressure. The residue was dissolved in ethyl acetate and washed successively with 1 M hydrochloric acid and brine, dried over magnesium sulphate, filtered and concentrated under reduced pressure to give a brown oil. Purification by column chromatography (silica gel, 10% methanol in dichloromethane) afforded the title compound as a yellow oil (24.74 g, 43%). $^1$H-NMR; δ (CDCl$_3$), 7.36 (5H, m), 5.12 (2H, m), 4.71 (2H, d, J=11.2 Hz) 2.94 (1H, m), 2.74 (1H, dd, J=8.3, 8.4 Hz), 2.33 (1H, m), 2.14 (2H, m),1.89–1.45 (6H, br m), 1.68 (3H, s) and 1.28 (2H, br m)

STEP G:

2S-Cyclopentyl-3R-[2,2-dimethyl-1 S-(methylcarbamoyl)propylcarbamoyl]-5-methyl-hex-5-enoic acid benzyl ester 2S-Cyclopentyl-3R-(2-methylallyl)succinic acid 4-benzyl ester (Step F) (38.2 g, 115.6 mmol) was dissolved in ethyl acetate (1 l) and to the solution were added EDC (24.4 g, 127.1 mmol) and HOBt (17.18 g, 127 mmol). The mixture was heated to reflux under an argon blanket for 2 hours before allowing to cool to room temperature. The organic solution was washed successively with 1 M hydrochloric acid and 1 M sodium carbonate solution, dried over magnesium sulphate and filtered. To the filtrate was added tert-leucine N-methylamide (18.3 g, 127.1 mmol) and the mixture was stirred and heated at reflux overnight under a blanket of argon. After cooling to room temperature the reaction mixture was washed with 1 M hydrochloric acid, and 1 M sodium carbonate solution, dried over magnesium sulphate, filtered and evaporated to give the desired product as a brown oil (45.1 g, 85%). $^1$H-NMR; δ (CDCl$_3$): 7.35 (5H, s), 6.68 (1H, m), 6.56 (1H, d, J=9.2 Hz), 5.11 (2H, m), 4.60 (2H, d, J=21 Hz), 4.32 (1H, d, J=9.2 Hz), 2.75 (3H, d, J=4.7 Hz), 2.31 (1 H, m), 2.09 (1H, m), 1.40–1.81 (10H, br m), 1.62 (3H, s), 1.23 (1H, m) and 0.97 (9H, s).

STEP H:

2S-Cyclopentyl-3R-[2,2-dimethyl-1S-(methylcarbamoyl)propylcarbamoyl]-5-methyl-hexanoic acid 2S-Cyclopentyl-3S-(2,2-dimethyl-1-methylcarbamoylpropylcarbamoyl)-5-methyl-hex-5-enoic acid benzyl ester (Step G) (47.4 g, 103.7 mmol) was dissolved in ethanol (1 l) and the solution was placed under a blanket of argon. 10% Palladium on charcoal (0.34 g) was added and a fine stream of hydrogen gas was passed through the suspension for 15 minutes and the solution was left under an atmosphere of hydrogen gas overnight with stirring. TLC showed that all the starting material had been consumed. The system was purged with argon and the catalyst was removed by filtration. Solvent was evaporated to give the desired product as a white foam (36 g, 94%). $^1$H-NMR; δ (CD$_3$OD), 7.94 (1H, d, J=4.6 Hz), 7.81 (1H, d, J=9.2 Hz), 4.19 (1H, d, J=9.2 Hz), 2.71 (1H, m), 0.89 (9H, s), 2.60 (3H, d, J=4.6 Hz), 2.51 (1H, dd, J=5.9, 6.0 Hz), 1.91 (1H, m), 1.15–1.80 (11H, br m), 0.79 (3H, d, J=6.5 Hz) and 0.72 (3H, d, J=6.5 Hz).

The compounds of Examples 3 to 17 were prepared by analogy with Example 1, starting from the appropriate cycloalkyl- or heterocyclylacetic acid and using the appropriate tert- leucine amide. Where the desired cycloalkyl- or heterocyclylacetic acids are not commercially available they were prepared by analogy with the method described below in Intermediate example 2 for (4-tert-butylcyclohexyl)acetic acid, which was used in the preparation of Example 13.

INTERMEDIATE EXAMPLE 2

4-tert-Butylcyclohexylacetic acid

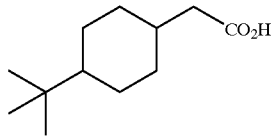

STEP A:

(4-tert-Butylcyclohexylidene)acetic acid methyl ester 4-tert-Butylcyclohexanone (8.62 g, 56 mmol) was dissolved in toluene (200 ml). Methoxycarbonylmethylenetriphenylphosphorane (56.1 g, 168 mmol) was added with stirring and the reaction mixture was heated under reflux for 3 days. The solvent was removed in vacuo. The residue was dissolved in hot hexanes (100 ml) and cooled to room temperature. The precipitate was filtered off and the filtrate was evaporated in vacuo to afford a yellow oil which was then purified by chromatography (silica gel, hexane/ethyl acetate, 2:1 as eluant) to give the title compound as an oil (10.78g, 92%). $^1$H-NMR; δ (CDCl$_3$) 5.60 (1H, s), 3.87 (1H, m), 3.69 (3H, s), 2.38–2.10 (2H, m), 2.03–1.77 (3H, m), 1.36–1.02 (3H, m) and 0.87 (9H, s).

STEP B:

(4-tert-Butylcyclohexyl)acetic acid methyl ester (4-tert-Butylcyclohexylidene)acetic acid methyl ester (10.78 g, 51.3 mmol) was dissolved in methanol (50 ml). Palladium hydroxide on carbon (1.0 g) was added and the reaction mixture was stirred at room temperature under an atmosphere of hydrogen overnight. The catalyst was then removed by filtration through celite and the filtrate was evaporated in vacuo to a clear oil (9.81 g, 91%). $^1$H-NMR; δ (CDCl$_3$) (as a mixture of cis-trans isomers), 3.67 (3H, s), 2.38 (1H, d, J=8 Hz), 2.18 (1H, d, 7 Hz), 1.85–1.44 (5H, m), 1.20–0.89 ( 5H, m) and 0.86 (9H, s).

STEP C:

(4-tert-Butylcyclohexyl)acetic acid (4-tert-Butylcyclohexyl)acetic acid methyl ester (9.81 g, 46.5 mmol) was dissolved in methanol 950 ml) and cooled on an ice bath. 2M Sodium hydroxide solution (50 ml, 100 mmol) was added with stirring. When addition was complete the reaction mixture was allowed to warm to room temperature and was stirred overnight. The methanol was evaporated in vacuo and the remaining aqueous phase was acidified to pH1 with 1M hydrochloric acid. The aqueous phase was then extracted with ethyl acetate(3x). The organic extracts were combined, dried over magnesium sulphate, filtered and evaporated to give a white solid, (8.66 g, 94%). $^1$H-NMR δ (CDCl$_3$) (as a mixture of cis-trans isomers), 2.43 (0.1 H, d, J=8Hz), 2.24 (0.9H, d, J =7 Hz), 1.92–1.47 (5H, m), 1.18–0.90 (5H, m) and 0.87 (9H, s).

EXAMPLE 3

2S-Cyclopentyl-3R-[2,2-dimethyl-1S-(pyridin-2-ylcarbamoyl)propylcarbamoyl]-5-methylhexanoic acid

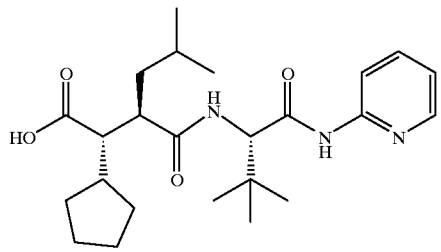

$^1$H-NMR; δ (CD$_3$OD). 8.18 (1H, m), 7.96 (1H, m), 7.66 (1H, m), 7.00 (1H, m), 4.41 (1H, s), 2.80–2.71 (1H, m), 2.49 (1H, m), 1.90 (1H, m), 1.71–1.19 (10H, m) 1.06 (1 H, m), 0.99 (9H, s), 0.80 (3H, d, J=6.4 Hz) and 0.68 (3H, d, J=6.5 Hz). $^{13}$C-NMR; δ (CD$_3$OD), 177.6, 177.2, 171.6, 152.7, 149.1, 139.4, 121.1, 115.6, 63.1, 54.1, 47.7, 42.3, 42.2, 35.3, 31.9, 29.7, 27.2, 27.1, 25.8, 24.4 and 22.0. IR: $v_{max}$(KBr): 3293, 3057, 2871, 1709, 1648, 1578, 1535, 1467, 1434, 1368, 1297, 1224, 1183, 777 cm$^{-1}$. Found: C 66.34%, H 8.68%, N 9.43%; C$_{24}$H$_{37}$N$_3$O$_4$ requires C 66.79%, H 8.64%, N 9.74%, O 14.83%.

EXAMPLE 4

2S-Cyclopentyl-3R-[2,2-dimethyl-1S-(thiazol-2-ylcarbamoyl)propylcarbamoyl]-5-methylhexanoic acid

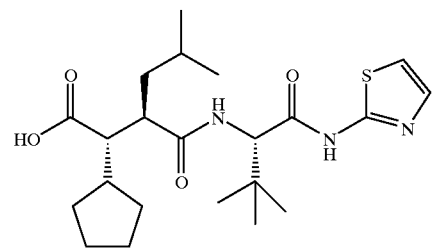

$^1$H-NMR; δ (CD$_3$OD, 4:1 mixture of diastereoisomers), 7.38 (0.2H, d, J=3.7 Hz), 7.34 (0.8H, d, J=3.5 Hz), 7.08 (0.2H, d, J=3.6 Hz), 7.00 (0.8H, d, J=3.5 Hz), 4.44 (0.8H, s), 4.42 (0.2H, s), 2.75 (1 H, m), 2.47 (1 H, dd, J=6.4, 6.6 Hz), 1.91–1.09 (11 H, br m), 1.02 (1.8H, s), 0.97 (7.2H, s), 0.87 (1 H, m), 0.78 (3H, d, J=6.3 Hz) and 0.66 (3H, d, J=6.5 Hz). $^{13}$C-NMR; δ (CD$_3$OD), 177.3, 170.7, 159.5, 138.4, 114.7, 62.4, 54.1, 47.5, 42.2, 35.2, 34.7, 31.9, 29.8, 27.1, 27.0, 26.1, 24.4 and 21.9.

EXAMPLE 5

2S-Cyclopentyl-3R-[2,2-dimethyl-1S-dimethylcarbamoylpropylcarbamoyl)-5-methylhexanoic acid

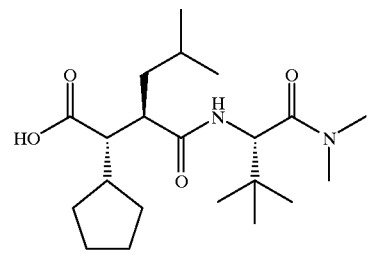

$^1$H-NMR; δ (CDCl$_3$), 7.86 (1H, m), 5.08 (1H, d, J=9.7 Hz), 3.19 (3H, s), 2.96 (3H, s), 2.8–2.7 (2H, m), 1.97 (1H, m), 1.95–1.40 (11 H, m), 0.98 (9H, s), 0.84 (3H, d, J=6.4 Hz) and 0.81 (3H, d, J=6.5 Hz).

EXAMPLE 6

3R-[1S-(Adamantan-1 -ylcarbamoyl)-2,2-dimethylpropylcarbamoyl]-2S-cyclopentyl-5-methylhexanoic acid

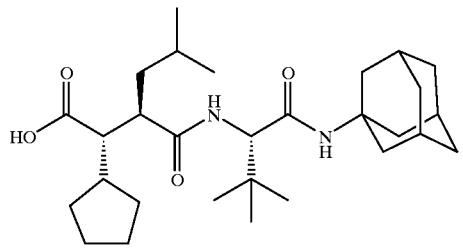

$^1$H-NMR; δ (CD$_3$OD), 7.58 (1H, d, J=9.3 Hz), 7.30 (1 H, br s), 4.12 (1H, d, J=9.4 Hz), 2.69 (1H, dt, J=3.2 and 10.7 Hz), 2.50 (1H, dd, J=5.9 and 10.2 Hz), 2.0–1.2 (27H, m), 0.9 (9H, s), 0.80 (3H, d, J=6.4 Hz) and 0.74 (3H, d, J=6.6 Hz).

EXAMPLE 7

2S-Cyclopentyl-3R-[2,2-dimethyl-1S-(1-methyl-1-phenylethylcarbamoyl) propylcarbamoyl]-5-methylhexanoic acid

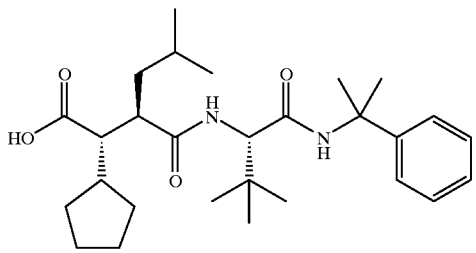

¹H-NMR δ (CDCl₃), 7.4–7.2 (6H, m), 6.45 (1 H, br s), 4.31 (1 H, d, J=9.5 Hz) 2.80–2.65 (2H, m), 1.97 (1H, m), 1.95–1.30 (17H, m), 0.99 (9H, s), 0.85 (3H, d, J=6.5 Hz) and 0.78 (3H, d, J=6.4 Hz).

EXAMPLE 8

2S-Cyclohexyl-3 R-[2,2-dimethyl-1S-(methylcarbamoyl)propylcarbamoyl]-5-methylhexanoic acid

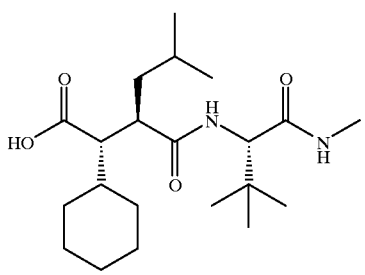

¹H-NMR: δ (CD₃OD), 7.95 (1H, m), 7.81 (1 H, br d, J=9.2 Hz), 4.21(1H, m), 2.81 (1H, dt. J=3.2 and 11.0 Hz), 2.60 (3H, m), 2.38 (1H, dd, J=3.8 and 10.9 Hz), 1.86 (1H, m), 1.77–0.95 (13H, m), 0.91 (9H,s), 0.80 (3H, d, J=6.4 Hz) and 0.71 (3H. d, J=6.5 Hz).

EXAMPLE 9

2S-Cyclohexyl-3R-[2,2-dimethyl-1S-(pyridin-2-ylcarbamoyl)propylcarbamoyl]-5-methylhexanoic acid

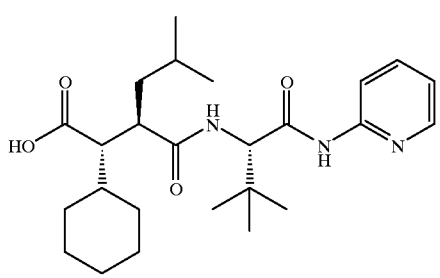

¹H-NMR; δ (CDCl₃), 10.32 (1H, brs), 8.46 (1H, d, J=8.7 Hz), 8.16 (1H, m), 7.83 (1H, m), 7.66 (1H, m), 7.15 (1H, m), 4.78 (1H, d, J=10.8 Hz), 3.01 (1H, m), 2.77 (1H, m), 2.03 (1H, m), 1.82–1.51 (10H, m), 1.36–1.21 (3H, m), 1.12 (9H, s), 0.77 (3H, d. J=6.4 Hz) and 0.72 (3H, d, J=6.4 Hz). ¹³C-NMR; δ (CDCl₃), 181.3, 172.7 169.2, 151.3, 145.3, 140.2, 119.8, 115.0, 62.8, 54.0, 46.9, 42.0, 37.6, 34.5, 32.4, 28.6, 27.0, 26.4, 26.3, 26.2, 23.9 and 22.5. IR:ν$_{max}$(KBr) 3299, 2929, 2853, 1703, 1674, 1578, 1531, 1484, 1368, 1297, 1231,1170, 777 cm⁻¹. Found: C 66.10%, H 8.79%, N 8.81%. C₂₅H₃₉N₃O₄.0.5H₂O requires C 66.05%, H 8.87%, N 9.24%.

EXAMPLE 10

2S-Cyclopropyl-3R-(1S-2,2-dimethyl-1-methylcarbamoylpropylcarbamoyl)-5-methylhexanoic acid

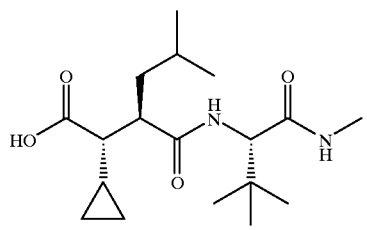

The title compound was used directly in Example 26 without characterisation.

EXAMPLE 11

3R-[2,2-dimethyl-1S-(methylcarbamoyl)propylcarbamoyl]-5-methyl-2S-(4-methylcyclohexyl)hexanoic acid

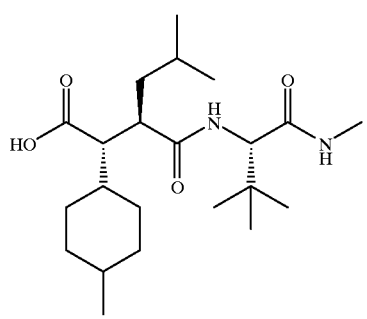

¹H-NMR; δ (CD₃OD), 4.21 (1H, s), 2.81 (1H, m), 2.59 (3H, s), 2.45 (1H, m), 1.81–1.23 (12H, m), 1.08 (1H, m), 0.91 (9H, s), 0.81 (6H, m) and 0.71 (3H, m). ¹³C-NMR; δ (CD₃OD), 179.5, 179.1, 175.5, 64.5, 57.9, 46.4, 45.2, 44.9, 41.9, 41.7, 39.2, 38.9, 37.7, 36.3, 35.9, 35.5, 35.2, 31.2, 26.8, 25.9, 24.5 and 20.6. IR:ν$_{max}$(KBr): 3287, 2926, 2855, 1712, 1635, 1553, 1464, 1370, 1247 cm⁻¹.

EXAMPLE 12

3R-[2,2-dimethyl-1S-(pyridin-2-ylcarbamoyl) propylcarbamoyl]-5-methyl-2S-(4-methylcyclohexyl) hexanoic acid

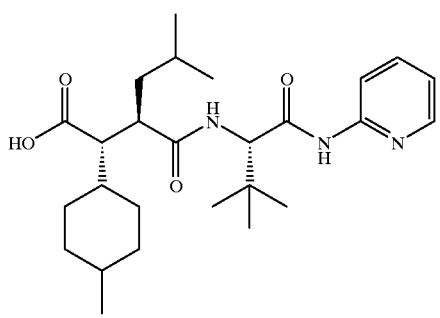

$^1$H-NMR; δ (CD$_3$OD), 8.18 (1H, m), 7.96 (1H, d, J=8.3 Hz), 7.66 (1H, m), 7.00 (1H, m), 4.49 (1H, s), 2.84 (1H, m), 2.47 (1H, m), 1.81–1.28 (12H, brm), 0.99 (9H, s) 0.80 (6H, t, J=6.6 Hz), 0.75 (1H, m) and 0.66 (3H, d, J=6.5 Hz). $^{13}$C-NMR; δ (CD$_3$OD), 179.7, 179.4, 173.9, 155.1, 151.5, 141.6, 123.5, 118.1, 65.1, 57.7, 46.4, 45.0, 41.9, 37.9, 36.3, 35.4, 31.3, 30.1, 26.8,26.1, 24.4 and 20.6. IR:ν$_{max}$(KBr) 3290, 2956, 2926, 1706, 1662,1635, 1576, 1533,1419, 1369, 1298 cm$^{-1}$.

EXAMPLE 13

2S-(4-tert-Butylcyclohexyl)-3R-[2,2-dimethyl-1S-(methylcarbamoyl)propylcarbamoyl]-5-methylhexanoic acid

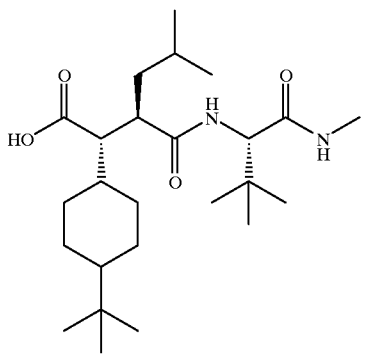

$^1$H-NMR; δ (CD$_3$OD, mixture of cyclohexyl cis-trans isomers) 4.20 (0.3H, s), 4.07 (0.7H, s), 2.60 (3H, s), 2.50 (1H, dd, J=6.9, 10.1 Hz), 2.40 (1H, 2 overlapping dt's), 1.80–1.41 (12H, m) 0.95 (3H, s), 0.92 (6H, s), 0.80 (1H, m), 0.78 (6H, s), 0.76 (6H, m) and 0.75 (3H, s).

EXAMPLE 14

3-[2,2-Dimethyl-1S-(methylcarbamoyl)propylcarbamoyl]-5-methyl-2S-(tetrahydrothiophen-3-yl)hexanoic acid

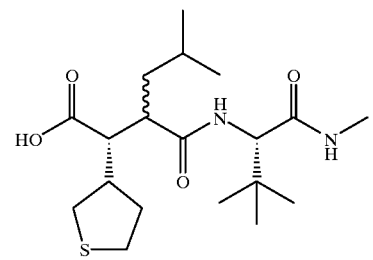

The title compound was used directly in Example 30 without characterisation.

EXAMPLE 15

2S-Cyclobutyl-3R-(2,2-dimethyl-1S-methylcarbamoylpropylcarbamoyl)-5-methylhexanoic acid

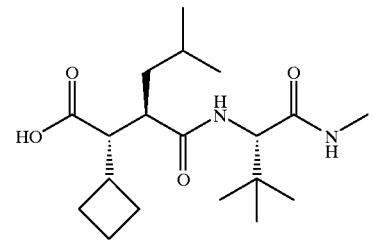

$^1$H-NMR; δ (CD$_3$OD, major diastereoisomer), 7.87 (1H, m), 7.69 (1H, m), 4.05 (1H, s), 2.60–2.53 (4H, m), 2.44 (1H, m), 1.85–1.25 (9H, m), 1.10–0.87 (10H, m), 0.79 (3H, d, J=6.4 Hz) and 0.72 (3H, d, J=6.6 Hz).

EXAMPLE 16

3R-[2,2-Dimethyl-1S-(methylcarbamoyl) propylcarbamoyl]-5-methyl-2S-(1-methyl piperidin-4-yl) hexanoic acid

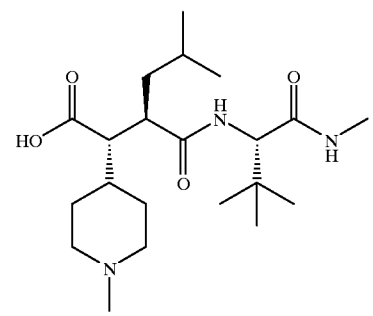

Off-white solid. m.p. 165–168° C. $^1$H-NMR; δ (CD$_3$OD), 4.16 (1H, s), 3.44–3.34 (2H, m), 2.70–2.49 (9H, m), 2.38 (1 H, dd, J=11.1, 3.3 Hz), 1.95–1.07 (7H, m), 0.99–0.87 (10H, m), 0.82 (3H, d, J=6.4 Hz) and 0.72 (3H, d, J=6.4 Hz). $^{13}$C-NMR; δ (CD$_3$OD), 181.3, 179.5, 175.4, 64.7, 59.1, 58.0, 48.8, 45.7, 45.6, 37.7, 37.4, 32.9, 29.8, 29.6, 28.4, 26.9 and 24.5.

EXAMPLE 17

2S-Cyclopentyl-3R-(2,2-dimethyl-1S-methylcarbamoylpropylcarbamoyl)undecanoic acid

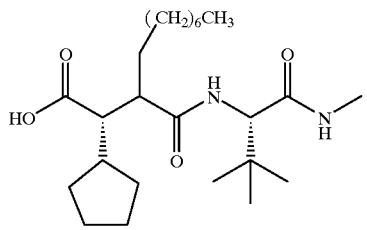

The title compound was prepared from decanoic acid, by analogy with Example 1, using (S)-phenylmethyl-2-oxazolidinone in Step A and 2-cyclopenten-1-ol in step E.

$^1$H-NMR; δ (CD$_3$OD), 7.84 (1H, d, J=9.3 Hz), 4.15 (1H, d, J=9.2 Hz), 2.60 (3H, s), 2.59 (1H, m), 1.90 (1H, m), 1.75–1.30 (9H, br m), 1.15 (14H. br m), 0.89 (9H, s) and 0.78 (3H, t, J=6.5 Hz). $^{13}$C-NMR; δ (CD$_3$OD), 179.8, 179.3, 175.6, 64.6, 55.4, 44.6, 37.5, 35.6, 35.5, 34.2, 33.1, 33.0, 32.7, 31.6, 30.7, 29.6, 28.4, 28.2, 26.1 and 16.9. IR; v$_{max}$ (KBr); 3292, 2958, 2857,1705, 1635, 1545, 1467, 1397, 1368, 1189 cm$^{-1}$.

EXAMPLE 18

2S-Cyclopentyl-N$^4$-[2,2-dimethyl-1S-(methylcarbamoyl) propyl]-N$^1$-hydroxy-3R-isobutylsuccinamide

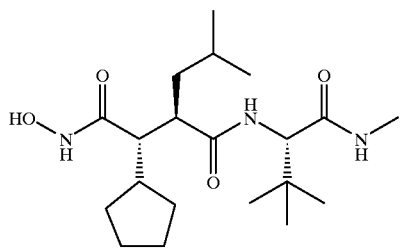

To a cooled solution of 2S-cyclopentyl-3S-[2,2-dimethyl-1S-(methylcarbamoyl)propyl carbamoyl]-5-methylhexanoic acid (Example 1) (17.45 g, 47.5 mmol) in DMF (180 ml) was added HOBt (7.7 g, 56.9 mmol) and EDC (10.9 g, 56.9 mmol). The mixture was stirred at 0° C. for 1 hour then at room temperature for 2 hours to ensure complete formation of the active ester. The solution was cooled back to 0° C. and hydroxylamine hydrochloride (4.95 g, 71.2 mmol) was added, followed by NMM (7.83 ml, 71.2 mmol) and the reaction mixture was allowed to warm to room temperature then stirred overnight. The solvent was removed in vacuo and the residue was partitioned between diethyl ether and water. The resulting precipitate was collected by filtration and slurried in ethyl acetate. The mixture was heated at reflux for 1 hour and then cooled to room temperature and the white solid was collected by filtration. Recrystallisation from methanol-DIPE afforded the title compound as a white solid (6.1 g, 35%; 12:1 mixture diastereomers) m.p. 220° C. (decomp). $^1$H-NMR; δ (CD$_3$OD, major diastereoisomer), 7.82 (1 H, d, J=8.9 Hz), 4.13 (1H, m), 2.71 (1H, ddd, J=10.8, 3.4, 3.4 Hz), 2.59 (3H, s), 2.17 (1H, dd, J=10.4, 6.0 Hz), 1.80 (1H, m), 1.67–1.25 (8H, m), 1.16–0.99 (3H, m), 0.91 (9H,s), 0.80 (3H, d, J=6.4 Hz) and 0.72 (3H, d, J=6.4 Hz). $^{13}$C-NMR; δ (CD$_3$OD), 177.1, 173.1, 172.5, 62.6, 50.9, 47.6, 42.7, 42.5, 35.0, 32.0, 29.6, 27.3, 27.0, 26.0, 25.6, 24.5, 22.0. IR; v$_{max}$ (KBr); 3376, 3294, 2957,1630, 1542, 1466, 1368 cm$^{-1}$. Found: C 62.58%, H 9.78%, N 10.95%; C$_{20}$H$_{37}$N$_3$O$_4$ requires C 62.63%, H 9.72%, N 10.96%.

The following compounds were similarly prepared from the appropriate carboxylic acids (Examples 3–17):

EXAMPLE 19

2S-Cyclopentyl-N$^4$-[2,2-dimethyl-1S-(pyridin-2-ylcarbamoyl)-propyl]-N$^1$-hydroxy-3R-isobutyl-succinamide

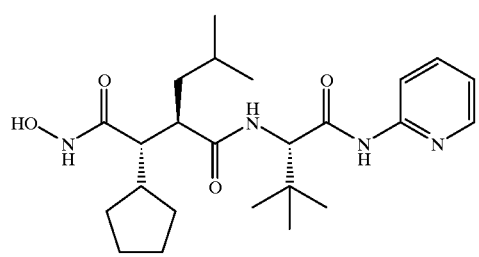

$^1$H-NMR; δ (CD$_3$OD), 8.18 (1H, m), 7.96 (1H, m), 7.66 (1H, m), 7.00 (1H, m), 4.39 (1H, s), 2.80 (1H, m), 2.17 (1H, m), 1.85 (1H, m), 1.68–1.33 (9H, m), 1.10–0.92 (11H, m), 0.80 (3H, d, J=6.4 Hz) and 0.66 (3H, d, J=6.5 Hz). $^{13}$C-NMR; δ (CD$_3$OD), 179.8, 175.0,173.9, 155.1, 151.5, 141.8, 123.4, 118.0, 65.8, 53.5, 49.8, 45.3, 44.9, 37.6, 34.5, 32.3, 29.6, 29.2, 28.0, 27.9, 26.9 and 24.3. IR: v$_{max}$(KBr) 3263, 2958, 2871, 1651, 1579, 1519, 1470, 1438, 1368, 1298, 1150, 1002 and 779 cm$^{-1}$. Found: C 63.65%, H 8.31%, N 11.73%; C$_{24}$H$_{38}$N$_4$O$_4$ requires C 64.55%, H 8.58%, N 12.55%, 0 14.33%.

EXAMPLE 20

2S-Cyclopentyl-N$^4$-[2,2-dimethyl-1S-(thiazol-2-yl) carbamoylpropyl]-N$^1$-hydroxy-3R-isobutylsuccinamide

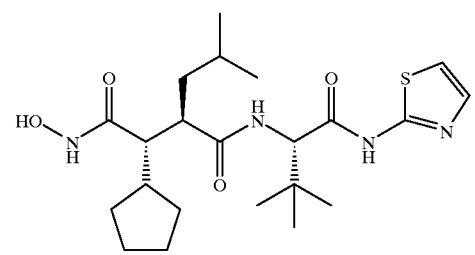

$^1$H-NMR; δ (CD$_3$OD), 7.33 (1H, d, J=3.6Hz.), 7.00 (1H, d, J=3.7Hz.), 4.41 (1H, s), 2.75 (1H, m), 2.14 (1H, dd, J=6.4, 6.5Hz.), 1.91–1.34(11H, m), 0.97 (9H, s), 0.86 (1H, m), 0.78 (3H, d, J=6.4Hz.), and 0.64 (3H, d, J=6.4Hz.). $^{13}$C-NMR; δ (CD$_3$OD), 177.6, 172.6, 170.6,138.4,114.6,62.7, 51.2, 47.2, 42.9,42.4, 35.0, 32.0, 30.1, 27.0. 26.8. 25.6, 24.4 and 21.9.

EXAMPLE 21

2S-Cyclopentyl-N$^4$-(1S-dimethylcarbamoyl-2,2-dimethylpropyl)-N$^1$-hydroxy-3R-isobutylsuccinamide

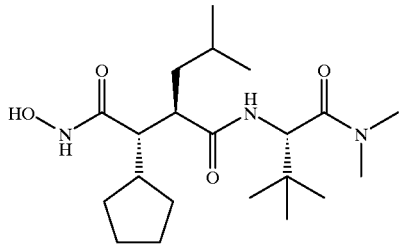

$^1$H-NMR; δ ((CD$_3$)$_2$SO), 10.39 (1H, d, J=1.7 Hz), 8.67 (1H, d, J=1.8 Hz), 7.84 (1H, d, J=8.8 Hz), 4.72 (1H, d, J=8.8 Hz), 3.07 (3H, s), 2.79 (3H, s), 2.77 (1H, m), 2.18 (1H, dd, J=5.3, 10.3 Hz), 1.89–1.21 (11H, m), 1.04 (1H, m), 0.94 (9H, s), 0.80 (3H, d, J=6.4 Hz) and 0.72 (3H, d, J=6.4 Hz). $^{13}$C-NMR; δ (DMSO), 179.3, 175.8, 174.4, 59.1, 53.6, 50.2, 46.0, 42.7, 40.1, 39.3, 35.4, 32.9, 31.5, 30.3, 29.3, 29.1 and 27.1. IR: v$_{max}$ (KBr) 3274, 2956, 1626,1507 cm$^{-1}$. Found: C 63.27%, H 10.06%, N 10.60%; C$_{21}$H$_{39}$N$_3$O$_4$ requires C 63.45%, H 9.89%, N 10.57%.

EXAMPLE 22

N$^4$-[1S-(Adamantan-1-ylcarbamoyl)-2,2-dimethylpropyl]-2S-cyclopentyl-N$^1$-hydroxy-3R-isobutylsuccinamide

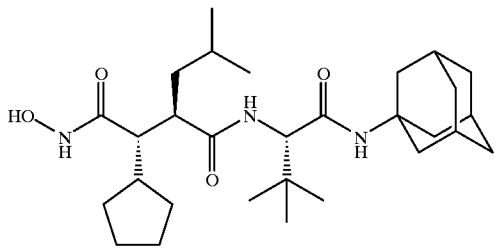

$^1$H-NMR; δ ((CD$_3$)$_2$SO), 10.39 (1H, s), 8.69 (1H, s), 7.62 (1H, d, J=9.3 Hz), 7.23 (1H, s), 4.18 (1H, d, J=9.5 Hz), 2.73 (1H, m), 2.22 (1H, dd. J=5.1. 10.5 Hz), 2.05–1.13 (22H, m), 1.19–0.93 (5H, m), 0.90 (9H, s), 0.83 (3H, d. J=6.3 Hz) and 0.75 (3H, d, J=7.0 Hz). $^{13}$C-NMR; δ (DMSO), 178.9, 174.3, 65.5. 55.9, 53.3, 50.8, 46.2, 45.9, 41.1, 36.7, 35.4, 33.9, 32.7, 31.8, 30.4, 29.3 and 27.0. IR: v$_{max}$ (KBr) 3275, 2948, 1678, 1522, 1367 cm$^{-1}$. Found: C 67.25%, H 9.99%, N 8.11%; C$_{29}$H$_{49}$N$_3$O$_4$.0.8H$_2$O requires C 67.22%, H 9.84%, N 8.11%.

EXAMPLE 23

2S-Cyclopentyl-N$^4$-[2,2-dimethyl-1S-(1-methyl-1-phenylethylcarbamoyl)propyl]-N$^1$-hydroxy-3R-isobutylsuccinamide

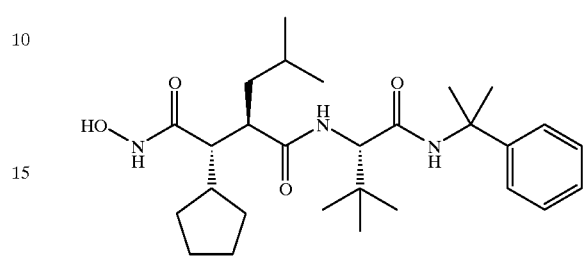

$^1$H-NMR; δ (CD$_3$OD), 8.06 (1 H, s), 7.66 (1H, d, J=9.2 Hz), 7.30–7.00 (5H, m), 4.23 (1H, d, J=9.0 Hz), 2.69 (1H, m), 2.17 (1H, dd, J=5.7, 10.5 Hz), 1.93–1.22 (10H, m), 1.58 (3H, s), 1.46 (3H, s), 1.20–0.88 (2H, m), 0.93 (9H, s), 0.73 (3H, J=6.5 Hz) and 0.72 (3H, d, J=6.4 Hz). $^{13}$C-NMR; δ (CD$_3$OD), 179.4,174.7, 173.8, 150.6, 131.5, 129.6, 128.4, 64.8, 59.4, 59.3, 53.2, 49.6, 45.1, 44.9, 37.6, 43.5, 33.0, 31.8. 31.1, 29.8, 29.2, 27.9. 27.2 and 24.1. IR: vmax(KBr) 3317, 2961, 1643, 1519 cm$^{-1}$. Found: C 68.60%, H 9.43%, N 8.46%; C$_{28}$H$_{45}$N$_3$O$_4$.0.2H$_2$O requires C 68.45%, H 9.31%, N 8.55%.

EXAMPLE 24

2S-Cyclohexyl-N$^4$-[2,2-dimethyl-1S-(methylcarbamoyl)propyl]-N$^1$-hydroxy-3R-isobutylsuccinamide

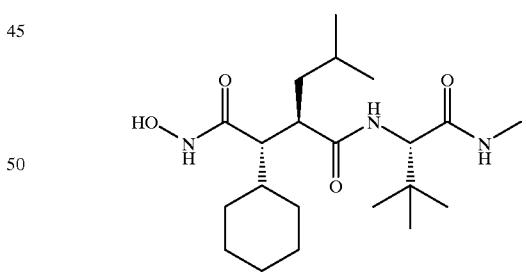

White solid. m.p. 230° C. (dec.). $^1$H-NMR; δ (CD$_3$OD), 7.86 (1H, m), 4.18 (1H, d, J=9.2 Hz), 2.79 (1H, m), 2.60 (3H, d, J=4.5 Hz), 2.05 (1H, dd, J 10.8, 3.7 Hz), 1.87 (1H, m), 1.63–1.31 (6H, m), 1.14–1.00 (7H, m), 0.92 (9H, s), 0.80 (3H, d, J=6.4 Hz) and 0.71 (3H, d, J=6.4 Hz). $^{13}$C-NMR; δ (CD$_3$OD), 179.2, 175.4, 174.1, 64.6, 55.5. 47.8, 46.0, 45.0, 42.3, 37.6, 36.2, 31.5, 30.4, 30.3, 29.9, 29.7, 29.4, 26.4, 26.7 and 24.4. IR (KBr) v$_{max}$ 3292, 2931, 2854, 1637,1559, 1513, 1466,1460, 1413, 1387, 1368, 1257,1195 and 1012 cm$^{-1}$.

EXAMPLE 25

2S-Cyclohexyl-N⁴-[2,2-dimethyl-1S-(pyridin-2-ylcarbamoyl)propyl]-N¹-hydroxy-3R-isobutylsuccinamide

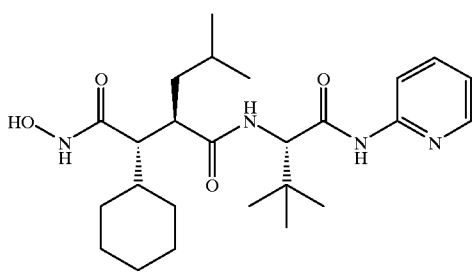

¹H-NMR; δ (CD$_3$OD), 8.19 (1H, m), 7.97 (1H, d, J=8.3 Hz), 7.66 (1H, m), 7.01 (1H, m), 4.48 (1H, s), 2.84 (1H, m), 2.08 (1H, dd, J=10.9, 3.8 Hz), 1.89 (1H, m). 1.63–1.25 (8H, m), 1.08–0.94 (14H. m), 0.79 (3H, d. J=6.4 Hz) and 0.65 (3H, d, J=6.4 Hz). ¹³C-NMR; δ (CD$_3$OD), 179.5,174.2, 173.8, 155.1, 151.5,141.8, 123.5.118.1, 65.2, 55.5, 47.7, 45.1,42.4, 37.9, 36.2, 31.6, 30.4, 30.3, 29.9, 29.7, 29.4, 26.9 and 24.4. IR: ν$_{max}$(KBr) 3322, 2927, 2852, 1657, 1578, 1516, 1434, 1368, 1297, 1216, 1194, 1173, 1151, 1012,884, 779 cm$^{-1}$. Found: C 65.04%, H 8.94%, N 11.94%; C$_{25}$H$_{40}$N$_4$O$_4$ requires C 64.93%, H 8.76%, N 12.12%.

EXAMPLE 26

2S-Cyclopropyl-N⁴-[2,2-dimethyl-1S-(methylcarbamoyl)propyl]-N¹-hydroxy-3R-isobutylsuccinamide

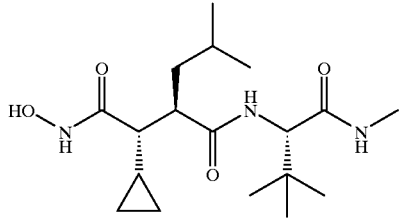

White solid. m.p. 200° C. (dec.). ¹H-NMR; δ (CD$_3$OD), 4.07, (1H, s), 2.79 (1H, m), 2.60 (3H, s), 1.61 (1H, m), 1.43–1.26 (3H, m), 0.93 (9H, s), 0.80 (3H, d, J=6.5 Hz), 0.72 (3H, d, J=6.5 Hz), 0.35 (1H, m), 0.25 (2H, m) and 0.06 (2H, m). ¹³C-NMR; δ (CD$_3$OD), 178.9, 175.6, 65.4, 54.7, 44.6, 37.1, 29.7, 29.4, 26.6, 26.4, 24.3, 15.8, 9.4 and 5.3. IR (KBr) ν$_{max}$ 3286, 2957, 2873, 1634, 1538, 1464, 1398, 1368, 1260, 1164 and 1022 cm$^{-1}$.

EXAMPLE 27

N¹-[2,2-Dimethyl-1S-(methylcarbamoyl)propyl]-N⁴-hydroxy-2S-isobutyl-3R-(4-methylcyclohexyl)succinamide

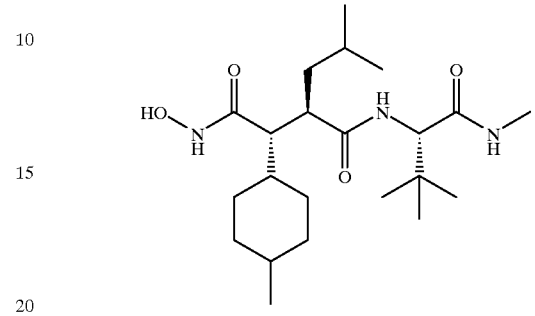

¹H-NMR; δ ((CD$_3$)$_2$SO), 10.33 (1H, s), 8.68 (1H, brs), 7.78 (2H, m), 4.21 (1H, d, J=8.9 Hz), 2.84 (2H, m), 2.54 (3H, d, J=4.4 Hz), 1.87–1.60 (3H, m), 1.32 (9H, m), 0.95 (1H, m), 0.91 (9H, s), 0.81 (6H, m) and 0.72 (3H, d, J=6.2 Hz). ¹³C-NMR; δ ((CD$_3$)$_2$SO), 178.9,178.8, 175.5, 173.9, 173.8, 65.2. 55.4, 48.6, 40.3, 38.9, 38.8, 37.3, 36.9, 36.5, 31.9, 31.8, 30.3, 29.0, 27.8, 26.9 and 22.6. IR:ν$_{max}$(KBr); 3299, 2955, 1640, 1530, 1466, 1369 cm$^{-1}$.

EXAMPLE 28

N¹-[2,2-Dimethyl-1S-(pyridin-2-ylcarbamoyl)propyl]-N⁴-hydroxy-2S-isobutyl-3R-(4-methylcyclohexylsuccinamide

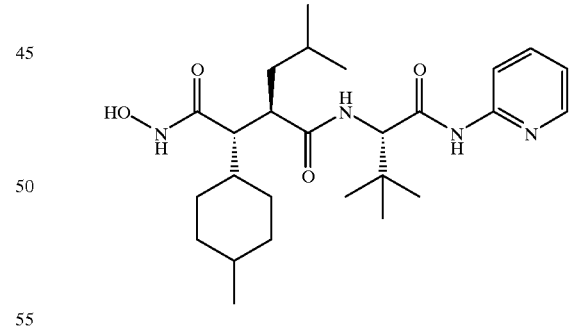

¹H-NMR; δ (CD$_3$OD), 8.19 (1H, m), 7.96 (1H, d, J=8.4 Hz), 7.69 (1H, m), 7.00 (1H, m), 4.49 (1H, m), 2.85 (1 H, m), 2.22 (1 H, m), 1.69–1.15 (12H, br m), 0.99 (9H, s), 0.79 (6H, m), 0.72 (1H, m) and 0.66 (3H, m). ¹³C-NMR; δ (CD$_3$OD), 179.6, 173.7, 155.1, 151.5, 141.6, 123.5,116.1, 65.4, 55.2, 48.0, 45.1, 41.9, 39.1, 37.6, 35.9, 35.2, 31.3, 29.7, 26.9, 26.0, 24.4, 20.7 and 16.8. IR:ν$_{max}$(KBr); 3269, 2956, 2870, 1653, 1579, 1521,1465, 1436, 1369, 1297 cm$^{-1}$.

EXAMPLE 29

2S-(4-tert-Butylcyclohexyl)-N$^4$-(2,2-Dimethyl-1S-methylcarbamoylpropyl)-N$^1$-hydroxy-3R-isobutylsuccinamide

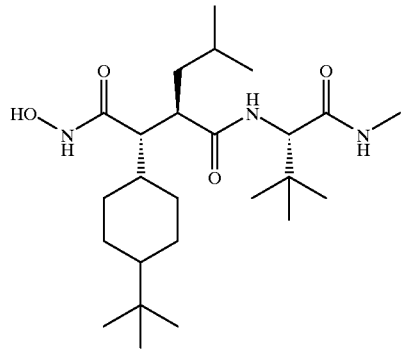

$^1$H-NMR; δ (CD$_3$OD), 4.19 (0.85H, s), 4.06 (0.15H, s), 2.79 (1H, m), 2.59 (3H, s), 2.39 (1H, dd. J=3.7, 4.1 Hz), 1.94–0.92 (12H, br m), 0.91 (7.7H, s), 0.88 (1.3H, s), 0.84 (1H, m), 0.79 (3H, d, J=6.5 Hz) and 0.72 (12H, m). $^{13}$C-NMR; δ (CD$_3$OD), 176.9, 176.7, 173.0, 62.1, 55.5, 52.7, 46.1, 45.6, 42.6, 41.3, 40.0, 39.7, 35.3, 34.0, 33.1, 31.9, 29.2, 28.8, 28.5, 28.4, 27.9, 27.3, 25.9, 24.4 and 22.0.

EXAMPLE 30

N$^1$-(2.2-Dimethyl-1S-methylcarbamoylpropyl)-N$^4$-hydroxy-2-isobutyl-3S-(tetrahydrothiophen-2-yl)succinamide

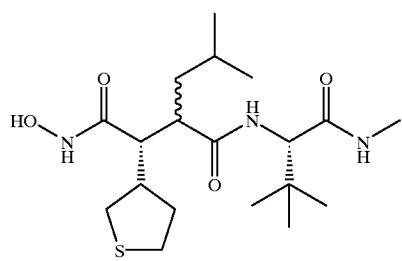

$^1$H-NMR δ (CD$_3$OD), 4.17 (1H, d, J=9.0 Hz), 2.59 (3H, s), 2.83 (1H, m), 2.77–2.02 (4H, br m), 1.70–0.94 (7H, br m), 0.90 (9H, s), 0.80 (3H, d, J=6.2 Hz) and 0.71 (3H, d, J=6.2 Hz). $^{13}$C-NMR; δ (CD$_3$OD, major diastereoisomer), 179.0, 175.3, 175.0, 64.9, 49.2, 49.9, 38.6, 37.6, 37.4, 36.1, 34.6, 33.2, 32.6, 29.7, 28.4, 26.9 and 24.4. IR; ν$_{max}$(KBr); 3315, 2958,1732, 1644, 1520, 1456, 1368, 1160 cm$^{-1}$. m/e (+FAB) 424.22 ([M+Na]$^+$), 402.24 ([M+H]$^+$).

EXAMPLE 31

2S-Cyclobutyl-N$^4$-(2,2-dimethyl-1S-methylcarbamoylpropyl)-N$^1$-hydroxy-3R-isobutylsuccinamide

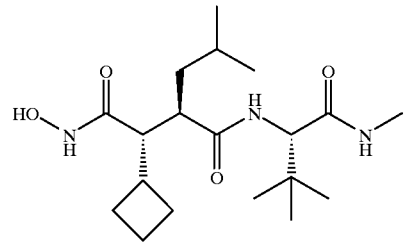

m.p. 245° C. (dec.). $^1$H-NMR; δ (CD$_3$OD), 3.99 (1 H, s), 2.61–2.51 (4H, m), 2.09 (1H, dd, J=10.3, 8.6 Hz), 1.85–1.57 (7H, m), 1.43–1.29 (2H, ni), 1.01–0.88 (10H, m), 0.78 (3H, d, J=6.5 Hz) and 0.71 (3H, d, J=6.5 Hz). $^{13}$C-NMR; δ (CD$_3$OD), 179.1, 175.5, 174.6, 65.5, 55.4, 49.0, 44.8, 40.8, 37.1, 31.6, 29.7, 29.5, 29.1, 28.4, 26.9, 24.3 and 21.3. IR:ν$_{max}$(KBr); 3293, 2959, 2871, 1637, 1525, 1469, 1413, 1386, 1369, 1213, 1167 and 1026 cm$^{-1}$. Found: C 61.57%, H 9.29%, N 11.28%; C$_{19}$H$_{35}$N$_3$O$_4$.0.1H$_2$O requires C 61.46%, H 9.56%, N 11.32%.

EXAMPLE 32

N$^1$-[2,2-Dimethyl-1S-(methylcarbamoyl)propyl]-N$^4$-hydroxy-2R-isobutyl-3S-(1-methylpiperidin-4-yl)succinamide

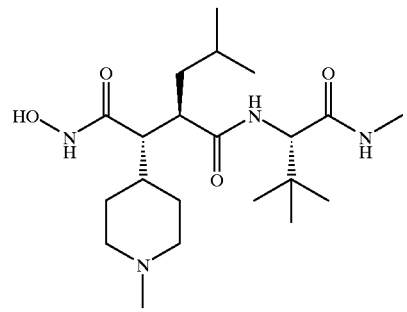

$^1$H-NMR; δ (CD$_3$OD), 4.17 (1H, s), 3.42 (2H, m), 2.82 (3H, m), 2.71 (3H, s), 2.60 (3H, s), 2.21 (1H, dd, J=10.9, 3.9 Hz), 2.13–1.25 (7H, m), 1.00 (1H, m), 0.91 (9H, s), 0.81 (3H, d, J=6.4 Hz) and 0.72 (3H, d, J=6.4 Hz). $^{13}$C-NMR; δ (CD$_3$OD), 176. 172.8, 170.6, 62.4, 56.1, 55.8, 50.9, 45.2, 43.8, 42.7, 35.3, 35.1, 29.9, 27.4, 26.9, 26.2, 26.0, 24.4 and 22.0.

EXAMPLE 33

2S-Cyclopentyl-$N^4$-(2,2-dimethyl-1S-methylcarbamoylpropyl)-$N^1$-hydroxy-3R-octylsuccinamide

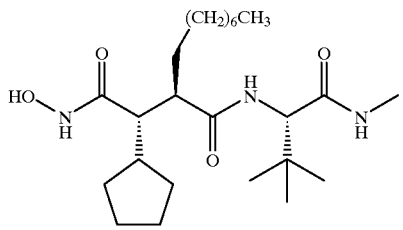

$^1$H-NMR; δ (CD$_3$OD), 4.13 (1H, s), 2.69 (1H, m), 2.60 (3H, s), 2.21 (1H, dd, J=10.6, 5.9 Hz), 1.90–1.20 (9H, br m), 1.15 (14H, br s), 0.90 (9H, s) and 0.78 (3H, t, J=6.4 Hz). $^{13}$C-NMR; δ (CD$_3$OD), 179.5, 175.6, 174.9, 64.8, 45.2, 37.4, 35.6, 35.4, 34.3, 33.2, 33.0, 32.7, 31.9, 30.6, 29.6, 28.4, 28.0, 27.9, 26.1 and 16.8. IR:ν$_{max}$(KBr) 3305.2929,2857, 1634, 1532, 1467, 1369, 1241, 1195, 1161 cm$^{-1}$.

We claim:

1. A compound of general formula (I)

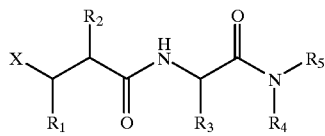

wherein:

X is a —CONHOH group;

R$_1$ is a cycloalkyl or a cycloalkenyl;

R$_2$ is a C$_1$–C$_{12}$ alkyl, C$_2$–C$_{12}$ alkenyl, C$_2$–C$_{12}$ alkynyl, phenyl(C$_1$–C$_6$, alkyl)-, cycloalkyl(C$_1$–C$_6$ alkyl)-, cycloalkenyl(C$_1$–C$_6$ alkyl)-, phenoxy(C$_1$–C$_6$ alkyl)-, phenyl(C$_1$–C$_6$ alkyl)O(C$_1$–C$_6$ alkyl)-, phenyl(C$_1$–C$_6$ alkyl)S(C$_1$–C$_6$ alkyl)-, or any one of which may be optionally substituted by C$_1$–C$_6$ alkyl, C$_1$–C$_6$ alkoxy, halo, cyano (—CN), phenyl, a substituted phenyl;

R$_3$ is the characterising group of a natural or non-natural α amino acid in which any functional groups may be protected, R$_4$ is (a) an optionally substituted cycloalkyl or cycloalkenyl ring or (b) a group —CHR$^x$R$^y$ wherein R$^x$ and R$^y$ each independently represents an optionally substituted phenyl ring which may be linked covalently to each other by a bond or by a C$_1$–C$_4$ alkylene or C$_2$–C$_4$ alkenylene bridge, or (c) a group of formula —(Z—O)$_n$—Z wherein Z is straight or branched C$_1$–C$_6$ alkyl optionally interrupted by one or more non-adjacent S and/or N atoms, n is an integer >1, and no continuous linear sequence of atoms in the group R$_4$ is >12, or (d) a straight or branched C$_1$–C$_6$ alkyl group, optionally interrupted by one or more non-adjacent S and/or N atoms, which is substituted by at least two substituents of formula —(Z)$_p$—(OZ)$_q$ wherein Z is straight or branched C$_1$–C$_6$ alkyl optionally interrupted by one or more non-adjacent S and/or N atoms, p is 0 or 1, q is 1 or 2, and no continuous linear sequence of atoms in the group R$_4$ is >12, or (e) hydrogen, C$_1$–C$_6$ alkyl, C$_1$–C$_4$ perfluoroalkyl, or a group D-(C$_1$–C$_6$ alkyl)- wherein D is hydroxy, C$_1$–C$_6$ alkoxy, C$_1$–C$_6$ alkylthio, acylamino, optionally substituted phenyl, NH$_2$, or mono- or di-(C$_1$–C$_6$ alkyl)amino;

or R$_3$ and R$_4$ taken together represent a divalent chain of formula —C(R$^a$)(R$^b$)—A—Alk—, wherein R$^a$ and R$^b$ are independently hydrogen or C$_1$–C$_6$ alkyl, A is a bond, —O—, —S—, —S—S—, —NH— or —NR$^a$— wherein R$^a$ is C$_1$–C$_6$ alkyl, and Alk is C$_1$–C$_6$ alkylene;

R$_5$ is hydrogen or a C$_1$–C$_6$ alkyl group;

or a salt, hydrate or solvate thereof.

2. A compound as claimed in claim 1 wherein the stereochemistry is as follows:

C atom carrying the R$_1$ and X groups—S,

C atom carrying the R$_2$ group—R,

C atom carrying the R$_3$ group—S.

3. A compound as claimed in any one of claims 1 to 2 wherein R$_2$ is n-pentyl, n-hexyl, n-heptyl, n-nonyl, n-decyl, phenylpropyl, 4-chlorophenylpropyl, 4-methylphenylpropyl, or 4-methoxyphenylpropyl.

4. A compound as claimed in any one of claims 1 to 2 wherein R$_2$ is iso-butyl, n-octyl, benzyloxypropyl, phenoxybutyl or 4-phenyl-phenylpropyl.

5. A compound as claimed in any one of claims 1, 2, 3 or 4 wherein R$_3$ is

C$_1$–C$_6$ alkyl, benzyl, 2,- 3-, or 4-hydroxybenzyl, 2,- 3-, or 4-benzyloxybenzyl, 2,- 3-, or 4-C$_1$–C$_6$ alkoxybenzyl, or benzyloxy(C$_1$–C$_6$alkyl)-; or the characterising group of a natural α amino acid, in which any functional group may be protected, any amino group may be acylated and any carboxyl group present may be amidated; or a group —[Alk]$_n$R$_6$ where Alk is a (C$_1$–C$_6$)alkyl or (C$_2$–C$_6$)alkenyl group optionally interrupted by one or more —O—, or —S— atoms or —N(R$_7$)— groups, n is 0 or 1, and R$_6$ is an optionally substituted cycloalkyl or cycloalkenyl group; or a benzyl group substituted in the phenyl ring by a group of formula —OCH$_2$COR$_8$ where R$_8$ is hydroxyl, amino, (C$_1$–C$_6$)alkoxy, phenyl(C$_1$–C$_6$)alkoxy, (C$_1$–C$_6$) alkylamino, di((C$_1$–C$_6$)alkyl)amino, phenyl(C$_1$–C$_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic((C$_1$–C$_6$)alkyl group, either being unsubstituted or mono- or di-substituted in the heterocyclic ring with halo, nitro, carboxy, (C$_1$–C$_6$)alkoxy, cyano, (C$_1$–C$_6$)alkanoyl, trifluoromethyl (C$_1$–C$_6$)alkyl, hydroxy, formyl, amino, (C$_1$–C$_6$)alkylamino, di-(C$_1$–C$_6$)alkylamino, mercapto, (C$_1$–C$_6$)alkylthio, hydroxy(C$_1$–C$_6$)alkyl, mercapto(C$_1$–C$_6$)alkyl or (C$_1$–C$_6$)alkylphenylmethyl; or a group —CR$_a$R$_b$R$_c$ in which:

each of R$_a$, R$_b$ and R$_c$ is independently hydrogen, (C$_1$–C$_6$)alkyl, (C$_2$–C$_6$)alkenyl, (C$_2$–C$_6$)alkynyl, phenyl(C$_1$–C$_6$)alkyl, (C$_3$–C$_8$)cycloalkyl; or R$_c$ is hydrogen, (C$_1$–C$_6$)alkyl, (C$_2$–C$_6$)alkenyl, (C$_2$–C$_6$) alkynyl, phenyl(C$_1$–C$_6$)alkyl, or (C$_3$–C$_8$)cycloalkyl, and R$_a$ and R$_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a cycloalkyl or heterocyclic ring, and R is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_5$)alkyl, —SO($C_1$–$C_6$)alkyl, —SO$_2$($C_1$–$C_6$) alkyl, —S($C_2$–$C_6$)alkenyl, —SO($C_2$–$C_6$)alkenyl, —SO$_2$($C_2$–$C_6$)alkenyl or a group —Q—W wherein Q represents a bond or —O—, —S—, —SO— or —SO$_2$— and W represents a phenyl phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH($C_1$–$C_6$)alkyl, —CONH($C_1$–$C_5$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$)alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl or benzyl.

6. A compound as claimed in any one of claims 1, 2, 3 or 4 wherein $R_3$ is iso-butyl, 1-benzylthio-1-methylethyl, or 1-methylthio-1-methylethyl.

7. A compound as claimed in any one of claims 1, 2, 3 or 4 wherein $R_3$ is t-butyl or 1-mercapto-1-methylethyl.

8. A compound as claimed in any one of claims 1, 2, or 3 to 7 wherein $R_4$ is cyclopropyl, cyclobutyl, cyclopentyl, cyclohexyl cycloheptyl, cyclooctyl or adamantyl;

optionally substituted phenyl, a group —CHR$^x$R$^y$ wherein R$^x$ and R$^y$ independently represent optionally substituted phenyl, 2-(2-methoxyethoxymethoxy)ethyl, 1,1-dimethyl-2-(2-methoxyethoxymethoxy)ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy)propyl, 2,2-dimethyl-3-(2-methoxyethoxymethoxy)propyl, 3-(2-methoxyethoxy)propyl, 2-methyl-2,2-di(2-methoxyethyl)propyl, 2-methyl-2,2-di(2-methoxyethyl)butyl, or 2-methyl-2,2-di(2-methoxymethyl)propyl;

ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl, or phenylpentyl.

9. A compound as claimed in any one of claims 1, 2, 3, 4, 5, 6 or 7 wherein $R_4$ is 3-methoxyphenyl, pyridin-2-yl, pyridin-3-yl, thiazol-2-yl, 4-ethoxycarbonylmethylthiazol-2-yl, 5-methyl-1,3,4-thiadiazol-2-yl or 4-tert-butylthiazol-2-yl.

10. A compound as claimed in any one of claims 1, 2, 3, 4, 5, 6 or 7 wherein $R_4$ is 2-(2-methoxyethoxy)ethyl.

11. A compound as claimed in any one of claims 1, 2, 3, 4, 5, 6 or 7 wherein $R_4$ is methyl.

12. A compound as claimed in any one of claims 1, 2, 3, 4, 5, 6 or 7 wherein $R_4$ is a group —CHR$^x$R$^y$ wherein R$^x$ and R$^y$ each independently represents phenyl or 4-chlorophenyl, or wherein $R_4$ is 9-H-fluoren-9-yl.

13. A compound as claimed in any one of claims 1, 2, or 3 to 12 wherein $R_5$ is hydrogen.

14. 2S-Cyclopentyl-N$^4$-[2,2-dimethyl-1S-(methylcarbamoyl)propyl)]-N $^1$-hydroxy-3R-isobutylsuccinamide, and salts solvates and hydrates thereof.

15. A compound selected from the group consisting of:

2S-cyclopentyl-N$^4$-(1S-dimethylcarbamoyl-2,2-dimethylpropyl)-N$^1$-hydroxy-3R-isobutylsuccinamide, N$^4$-[1S-(adamantan-1-ylcarbamoyl)-2,2-dimethylpropyl]-2S-cyclopentyl-N$^1$-hydroxy-3R-isobutylsuccinamide, 2S-cyclopentyl-N$^4$-[2,2-dimethyl-1S-(1-methyl-1-phenylethylcarbamoyl)propyl]-N$^1$-hydroxy-3R-isobutylsuccinamide, 2S-cyclohexyl-N$^4$-[2,2-dimethyl-1S-(methylcarbamoyl)propyl]-N$^1$-hydroxy-3R-isobutylsuccinamide, 2S-cyclopropyl-N$^4$-[2,2-dimethyl-1S-(methylcarbamoyl)propyl]-N$^1$-hydroxy-3R-isobutylsuccinamide, N$^1$-[2,2-dimethyl-1S-(methylcarbamoyl)propyl]-N$^4$-hydroxy-2S-isobutyl-3R-(4-methylcyclohexyl)succinamide, 2S-(4-tert-butylcyclohexyl)-N$^4$-(2,2-Dimethyl-1S-methylcarbamoylpropyl)-N$^1$-hydroxy-3R-isobutylsuccinamide, 2S-cyclobutyl-N$^4$-(2,2-dimethyl-1S-methylcarbamoylpropyl)-N$^1$-hydroxy-3R-isobutylsuccinamide, 2S-cyclopentyl-N$^4$-(2,2-dimethyl-1S-methylcarbamoylpropyl)-N$^1$-hydroxy-3R-octylsuccinamide, and salts solvates and hydrates thereof.

16. A pharmaceutical composition comprising a compound as claimed in any one of claims 1, 2, 3 to 7, or 14 to 15, together with a pharmaceutically acceptable carrier.

17. A composition as claimed in claim 16, adapted for oral administration.

* * * * *

UNITED STATES PATENT AND TRADEMARK OFFICE
CERTIFICATE OF CORRECTION

PATENT NO.:  6,127,427
DATED:       October 3, 2000
INVENTOR:    Fionna Mitchell MARTIN *et al.*

It is certified that errors appear in the above-identified patent and that said Letters Patent is hereby corrected as shown below:

In Claim 1, column 35, line 43:
    ",a" has been replaced with --,or--.

In Claim 5, column 36, line 35:
    "groups, n" has been replaced with --groups [where $R_7$ is a hydrogen atom or a $(C_1-C_6)$alkyl group], n--.

Column 37, line 9:
        "R" has been changed to --$R_c$--.

Column 37, line 12:
        "$C_1-C_5$" has been changed to --$C_1-C_6$--.

Column 37, line 24:
        "$C_1-C_5$ alkyl" has been changed to --$C_1-C_6$ alkyl--.

In Claim 9, column 38, line 6:
    "pyridin-2-yl, pyridin-3-yl, thiazol-2-yl, 4-ethoxycoarbonylmethylthiazol-2-yl, 5-methyl-1,3,4-thiadiazol-2-yl or 4-tert-butylthiazol-2-yl" has been removed from the claim.

UNITED STATES PATENT AND TRADEMARK OFFICE
CERTIFICATE OF CORRECTION

PATENT NO. : 6,127,427
DATED : October 3, 2000
INVENTOR(S) : Fionna Mitchell Martin, et. al.

It is certified that error appears in the above-identified patent and that said Letters Patent is hereby corrected as shown below:

In Claim 16, column 38, line 51:
"7" has been changed to --13--.

Signed and Sealed this

Twenty-second Day of May, 2001

*Attest:*

NICHOLAS P. GODICI

*Attesting Officer*     *Acting Director of the United States Patent and Trademark Office*